United States Patent
Sislian et al.

(10) Patent No.: US 10,080,857 B2
(45) Date of Patent: Sep. 25, 2018

(54) SYSTEM FOR BREATH SAMPLE COLLECTION AND ANALYSIS

(71) Applicant: Deton Corp., Pasadena, CA (US)

(72) Inventors: Patrick Sislian, Toluca Lake, CA (US); Ramzi Nasr, Falls Church, VA (US); Laura Luhede, Bremen (DE); Stephen Allen Chapman, Pasadena, CA (US)

(73) Assignee: Deton Corp., Pasadena, CA (US)

( * ) Notice: Subject to any disclaimer, the term of this patent is extended or adjusted under 35 U.S.C. 154(b) by 438 days.

(21) Appl. No.: 14/773,952

(22) PCT Filed: Mar. 12, 2014

(86) PCT No.: PCT/US2014/024682
§ 371 (c)(1),
(2) Date: Sep. 9, 2015

(87) PCT Pub. No.: WO2014/165184
PCT Pub. Date: Oct. 9, 2014

(65) Prior Publication Data
US 2016/0022946 A1    Jan. 28, 2016

Related U.S. Application Data

(60) Provisional application No. 61/778,360, filed on Mar. 12, 2013, provisional application No. 61/916,159, filed on Dec. 14, 2013.

(51) Int. Cl.
*A61B 5/08* (2006.01)
*A61N 1/22* (2006.01)
(Continued)

(52) U.S. Cl.
CPC .......... *A61M 16/085* (2014.02); *A61B 5/082* (2013.01); *A61B 5/097* (2013.01); *A61B 10/00* (2013.01);
(Continued)

(58) Field of Classification Search
CPC .............. A61M 16/085; A61M 16/201; A61M 16/105; A61M 16/208; A61M 2205/0216;
(Continued)

(56) References Cited

U.S. PATENT DOCUMENTS 3,760,831 A    9/1973   Colvin
3,858,573 A    1/1975   Ryan
(Continued)

FOREIGN PATENT DOCUMENTS

CN       1676173 A     10/2005
CN     101379388 A      3/2009
(Continued)

OTHER PUBLICATIONS

International Preliminary Report on Patentability for International Application PCT/US14/24682, dated Sep. 15, 2015, dated Sep. 24, 2015, 11 Pgs.
(Continued)

*Primary Examiner* — Navin Natnithithadha
(74) *Attorney, Agent, or Firm* — KPPB LLP

(57) ABSTRACT

Systems and methods for collecting samples from a patient for diagnosis are provided. In many embodiments, the sample collection and analysis system concentrates particles emanating from a patient's cough, sneeze, or breathe in a sample for the diagnosis of a respiratory tract infection or other ailment of the patient. The sample collection and analysis system has a pre-collection assembly (that is patient interface, a collector in fluid communication with a sample reservoir that function in combination to: efficiently capture the volume of air expelled from the subject, direct the expelled air towards a sample reservoir, and separate the desired particle sizes from the expelled air into the sample reservoir.

25 Claims, 14 Drawing Sheets

(51) Int. Cl.
*A61B 5/097* (2006.01)
*A61B 10/00* (2006.01)
*C12N 1/06* (2006.01)
*G01N 33/497* (2006.01)
*A61M 16/08* (2006.01)
*G01N 1/22* (2006.01)
*A61M 16/20* (2006.01)
*A61M 16/10* (2006.01)

(52) U.S. Cl.
CPC ....... *A61B 10/0051* (2013.01); *A61M 16/105* (2013.01); *A61M 16/201* (2014.02); *A61M 16/208* (2013.01); *G01N 1/2202* (2013.01); *A61B 2010/0083* (2013.01); *A61B 2010/0087* (2013.01); *A61M 2205/0216* (2013.01); *A61M 2205/123* (2013.01); *A61M 2205/58* (2013.01); *A61M 2205/7545* (2013.01); *C12N 1/06* (2013.01); *G01N 33/497* (2013.01); *G01N 2001/2244* (2013.01)

(58) Field of Classification Search
CPC .... A61M 2205/123; A61M 2205/7545; A61B 5/082; A61B 5/097; A61B 10/00; A61B 10/0051; A61B 2010/0083; A61B 2010/0087; G01N 1/2202; G01N 33/497; G01N 2001/2244; C12N 1/06
USPC .................................................. 600/529–543
See application file for complete search history.

(56) References Cited

U.S. PATENT DOCUMENTS

| 3,880,591 | A  | 4/1975  | Burroughs et al. |
|-----------|----|---------|------------------|
| 4,133,202 | A  | 1/1979  | Marple           |
| 4,297,871 | A  | 11/1981 | Wright et al.    |
| 4,558,708 | A  | 12/1985 | Labuda et al.    |
| 4,572,208 | A  | 2/1986  | Cutler et al.    |
| 4,640,140 | A  | 2/1987  | Burghoffer et al.|
| 4,678,488 | A  | 7/1987  | Howard et al.    |
| 5,042,501 | A  | 8/1991  | Kenny et al.     |
| 5,046,491 | A  | 9/1991  | Derrick          |
| 5,081,871 | A  | 1/1992  | Glaser           |
| 5,211,181 | A  | 5/1993  | Delente          |
| 5,253,641 | A  | 10/1993 | Choate           |
| 5,372,126 | A  | 12/1994 | Blau             |
| 5,409,014 | A  | 4/1995  | Napoli et al.    |
| 5,465,728 | A  | 11/1995 | Phillips et al.  |
| 5,533,513 | A  | 7/1996  | Ueda et al.      |
| 5,573,005 | A  | 11/1996 | Ueda et al.      |
| 5,739,412 | A  | 4/1998  | Stock et al.     |
| 5,787,885 | A  | 8/1998  | Lemelson         |
| 5,826,577 | A  | 10/1998 | Perroz et al.    |
| 5,855,652 | A  | 1/1999  | Talley           |
| 5,902,385 | A  | 5/1999  | Willeke et al.   |
| 5,904,752 | A  | 5/1999  | Willeke          |
| 6,053,874 | A  | 4/2000  | Kharitonov et al.|
| 6,217,636 | B1 | 4/2001  | McFarland        |
| 6,468,330 | B1 | 10/2002 | Irving et al.    |
| 6,520,034 | B1 | 2/2003  | Masquelier et al.|
| 6,582,376 | B2 | 6/2003  | Baghdassarian    |
| 6,585,661 | B1 | 7/2003  | Hunt et al.      |
| 6,723,056 | B1 | 4/2004  | Alving et al.    |
| 6,726,637 | B2 | 4/2004  | Phillips         |
| 6,729,196 | B2 | 5/2004  | Moler et al.     |
| 6,854,344 | B2 | 2/2005  | Cornish et al.   |
| 7,073,402 | B2 | 7/2006  | Trakumas et al.  |
| 7,118,537 | B2 | 10/2006 | Baddour          |
| 7,153,272 | B2 | 12/2006 | Talton           |
| 7,282,032 | B2 | 10/2007 | Miller           |
| 7,297,120 | B2 | 11/2007 | Tsukashima et al.|
| 7,364,553 | B2 | 4/2008  | Paz et al.       |
| 7,377,901 | B2 | 5/2008  | Djupesland et al.|
| 7,384,793 | B2 | 6/2008  | McCash et al.    |
| 7,547,285 | B2 | 6/2009  | Kline            |
| 7,594,894 | B2 | 9/2009  | Cardell et al.   |
| 7,631,567 | B1 | 12/2009 | Hill             |
| 7,779,840 | B2 | 8/2010  | Acker et al.     |
| 7,897,400 | B2 | 3/2011  | Timmins et al.   |
| 7,964,389 | B2 | 6/2011  | Chen             |
| 8,002,712 | B2 | 8/2011  | Meka et al.      |
| 8,240,187 | B2 | 8/2012  | Colman et al.    |
| 2001/0029793 | A1 | 10/2001 | Moler et al.   |
| 2002/0134137 | A1 | 9/2002  | Ondov et al.   |
| 2002/0157621 | A1 | 10/2002 | Lefrancois et al. |
| 2003/0153844 | A1 | 8/2003  | Smith et al.   |
| 2004/0024330 | A1 | 2/2004  | Djupesland et al. |
| 2004/0161804 | A1 | 8/2004  | McCash et al.  |
| 2004/0162500 | A1 | 8/2004  | Kline          |
| 2004/0232052 | A1 | 11/2004 | Call et al.    |
| 2004/0249300 | A1 | 12/2004 | Miller         |
| 2005/0065446 | A1 | 3/2005  | Talton         |
| 2005/0085740 | A1 | 4/2005  | Davis et al.   |
| 2005/0137491 | A1 | 6/2005  | Paz et al.     |
| 2006/0195040 | A1 | 8/2006  | Nason et al.   |
| 2006/0238757 | A1 | 10/2006 | Silcott et al. |
| 2007/0173731 | A1 | 7/2007  | Meka et al.    |
| 2007/0199567 | A1 | 8/2007  | Kanzer         |
| 2007/0235100 | A1 | 10/2007 | Tomerlin et al.|
| 2008/0038207 | A1 | 2/2008  | Edwards et al. |
| 2008/0214947 | A1 | 9/2008  | Hunt           |
| 2009/0187113 | A1 | 7/2009  | Friedman et al.|
| 2009/0255535 | A1 | 10/2009 | Kanzer         |
| 2010/0159575 | A1 | 6/2010  | Chen           |
| 2011/0105856 | A1 | 5/2011  | Haines et al.  |
| 2012/0004571 | A1 | 1/2012  | Ku et al.      |
| 2012/0168634 | A1 | 7/2012  | Egen et al.    |
| 2012/0203126 | A1 | 8/2012  | Kahlman et al. |
| 2013/0217029 | A1 | 8/2013  | Sislian et al. |

FOREIGN PATENT DOCUMENTS

| CN | 101466436 A | 6/2009 |
| CN | 101742964 A | 6/2010 |
| CN | 102264404 A | 11/2011 |
| CN | 102498398 A | 6/2012 |
| CN | 102596029 A | 7/2012 |
| CN | 103119417 A | 5/2013 |
| CN | 105339486 A | 2/2016 |
| DE | 19718924 A1 | 10/1998 |
| EP | 0302681 A2 | 2/1989 |
| EP | 2104451 A2 | 9/2009 |
| EP | 2379128 A2 | 10/2011 |
| EP | 2591331 A1 | 5/2013 |
| EP | 2970858 A1 | 1/2016 |
| IN | 803/CHENP/2013 A | 5/2016 |
| JP | 0854389 A | 2/1996 |
| JP | 2005538819 A | 12/2005 |
| JP | 2016512431 A | 4/2016 |
| WO | 2007120644 A2 | 10/2007 |
| WO | 2012006250 A1 | 1/2012 |
| WO | 2012120140 A1 | 9/2012 |
| WO | 2014165184 A1 | 10/2014 |

OTHER PUBLICATIONS

International Search Report and Written Opinion for International Application PCT/US14/24682, completed Jul. 10, 2014, dated Aug. 11, 2014 13 Pgs.

Stewart, "Effect of impact stress on microbial recovery on an agar surface.", Applied and Environmental Microbiology, Apr. 1995, p. 1234, Apr. 1995, 1232-1239.

Extended European Search Report for European Application No. 14780070.0, Search completed Oct. 12, 2016, dated Oct. 19, 2016, 13 Pgs.

Biswas et al., "The particle trap impactor", Journal of Aerosol Science, vol. 19, No. 1, Feb. 1, 1988, pp. 113-121.

Cash et al., "A Variable Order Runge-Kutta Method for Initial Value Problems with Rapidly Varying Right-Hand Sides", ACM Transactions of Mathematical Software, Sep. 1990, No. 16, No. 3, pp. 201-222.

(56) References Cited

OTHER PUBLICATIONS

Clayden et al., "HIV, Hepatitis C Virus (HCV), and Tuberculosis Drugs, Diagnostics, Vaccines, and Preventive Technologies in Development, Jul. 2011 Pipeline Report", Drugs, Diagnostics, Vaccines & Preventive Technologies in Development, 2012, 162 pgs. (presented in two parts).

Clift et al., "Bubbles, Drops, and Particles", Academic Press, 1978, 394 pgs. (presented in two parts).

Cunningham et al., "Diagnostics for tuberculosis: global demand and market potential", World Health Organization, 2006, 205 pgs.

Dunlap et al., "Diagnostic Standards and Classification of Tuberculosis in Adults and Children", American Journal of Respiratory and Critical Care Medicine, 2000, vol. 161, pp. 1376-1395.

Fennelly et al., "Cough-generated Aerosols of *Mycobacterium tuberculosis*", American Journal of Respiratory and Critical Care Medicine, 169(5):604-609, Dec. 4, 2003.

Fennelly et al., "Variability of Infectious Aerosols Produced During Coughing by Patients with Pulmonary Tuberculosis", American Journal of Respiratory and Critical Care Medicine, Mar. 10, 2012, vol. 186, Issue 5, pp. 450-457.

Jones-Lopez et al., "Cough Aerosols of *Mycobacterium tuberculosis* in the Prediction of Incident Tuberculosis Disease in Household Contacts", American Journal of Respiratory and Critical care medicine, 2013, vol. 187, No. 9, pp. 1017-1015.

Lindsley et al., "Measurements of Airborne Influenza Virus in Aerosol Particles from Human Coughs", PloS ONE, Nov. 2010, vol. 5, Issue 11, pp. e15100-1-e15100-6.

Peres et al., "Comparison of two concentrations of NALC—NaOH for decontamination of sputum for mycobacterial culture", Int. J. Tuberc. Lung Dis., Jul. 3, 2009, vol. 13, No. 12, pp. 1572-1575.

Pratt et al., "Trends in tuberculosis—United States. 2008", Center of Disease Control and Prevention, Mar. 20, 2009, vol. 58, No. 10-246-253.

Rader et al., "Effect of Ultra-Stokesian Drag and Particle Interception on Impaction Characteristics," Aerosol Science and Technology, 1985, vol. 4, pp. 141-156.

Sakundarno et al., "Insufficient quality of sputum submitted for tuberculosis diagnosis and associated factors, in Klaten district, Indonesia", BMC Pulmonary Medicine, May 8, 2009, vol. 9, No. 16, pp. 1-11.

Scholz et al., "PneumoniaCheck: A Device for Sampling Lower Airway Aerosols", Journal of Medical Devices, Dec. 2010, vol. 4, pp. 041005-1-041005-6.

Sislian et al., "Bacterial aerosol neutralization by aerodynamic shocks using an impactor system: Experimental results for *E. coli* and analysis", Chemical Engineering Science, Nov. 4, 2009, vol. 54, pp. 1490-1502.
Wainwright et al., "Cough-generated aerosols of Pseudomonas aeruginosa and other Gram-negative bacteria from patients with cystic fibrosis", THORAX, Jul. 1, 2009, vol. 64, pp. 926-931.
WHO, "Global Tuberculosis Report 2012", WHO, 2012, 98 pgs.
WHO, "Guidance for National Tuberculosis Programmes on the management of tuberculosis in children, Chapter 1: Introduction and diagnosis of tuberculosis in children", International Journal of Tuberculosis and Lung Disease, 2006, vol. 10, No. 10, pp. 1091-1097.
Helb et al., "Rapid Detection of *Mycobacterium tuberculosis* and Rifampin Resistance by Use of On-Demand, Near-Patient Technology", Journal of Clinical Microbiology, vol. 48, No. 1, Jan. 2010, pp. 229-237, Published Online Oct. 28, 2009, doi: 10.1128/JCM.01463-09.
Hering et al., "Design and Evaluation of New Low-Pressure Impactor. 2", Environmental Science and Technology, 1979, vol. 13, No. 2, pp. 184-188.
Hering et al., "Design and Evaluation of New Low-Pressure Impactor. I.", Environmental Science and Technology, 1978, vol. 12, No. 6, pp. 667-673.
Johnson et al., "The Mechanism of Breath Aerosol Formation", Journal of Aerosol Medicine and Pulmonary Drug Delivery, vol. 22, Issue 3, Sep. 14, 2009, pp. 229-237, https://doi.org/10.1089/jamp.2008.0720.
Jones-Lopez et al., "Cough Aerosols of *Mycobacterium tuberculosis* Predict New Infection. A Household Contact Study", American Journal of Respiratory and Critical Care Medicine, vol. 187, No. 9, May 1, 2013, pp. 1007-1015, https://doi.org/10.1164/rccm.201208-1422OC.
Joseph et al., "Breakup of a liquid drop suddenly exposed to a high-speed airstream", International Journal of Multiphase Flow, 1999, vol. 25, No. 6-7, pp. 1263-1303.
Keeler et al., "Reducing the global burden of tuberculosis: the contribution of improved diagnostics", Nature, Nov. 22, 2006, pp. 49-57, doi:10.1038/nature05446.
Khan et al., "Diagnosis of tuberculosis in children: increased need for better methods", Emerging Infectious Diseases, vol. 1, No. 4, Oct.-Dec. 1995, pp. 115-123, doi: 10.3201/eid0104.950402.
Klevens et al., "Estimating Health Care-Associated Infections and Deaths in U.S. Hospitals, 2002", Public Health Reports, Mar.-Apr. 2007, vol. 122, pp. 160-166.
Korteweg et al., "Pathology, Molecular Biology, and Pathogenesis of Avian Influenza A (H5N1) Infection in Humans", The American Journal of Pathology, May 2008, vol. 172, Issue 5, pp. 1155-1170, DOI: https://doi.org/10.2353/ajpath.2008.070791.
Kuiken et al., "Pathology of human influenza revisited", Vaccine, vol. 26, Supplement 4, Sep. 12, 2008, pp. D59-D66, https://doi.org/10.1016/j.vaccine.2008.07.025.
Lieberman et al., "Identification of Respiratory Viruses in Adults: Nasopharyngeal versus Oropharyngeal Sampling", Journal of Clinical Microbiology, vol. 47, No. 11, Nov. 2009, pp. 3439-3443, published online Sep. 2, 2009, doi: 10.1128/JCM.00886-09.
Lin et al., "Survival of Airborne Microorganisms During Swirling Aerosol Collection", Aerosol Science and Technology, vol. 32, Issue 3, 2000, pp. 184-196, https://doi.org/10.1080/02786820030372.
Lindsley et al., "A two-stage cyclone using microcentrifuge tubes for personal bioaerosol sampling", Journal of Environmental Monitoring, vol. 8, Issue 11, 2006, pp. 1136-1142, DOI:10.1039/B609083D.
Marentis et al., "Microfluidic Sonicator for Real-Time Disruption of Eukaryotic Cells and Bacterial Spores for DNA Analysis", Ultrasound in Medicine and Biology, 2005, vol. 31, No. 9, pp. 1265-1277.
Marple et al., "Virtual impactors: a theoretical study", Environmental Science & Technology, Aug. 1980, vol. 14, No. 8, pp. 976-985, DOI: 10.1021/es60168a019.
Martens-Habbena et al., "Sensitive Determination of Microbial Growth by Nucleic Acid Staining in Aqueous Suspension", Applied and Environmental Microbiology, Jan. 2006, vol. 72, No. 1, pp. 87-95.
McNerney et al., "Field test of a novel detection device for *Mycobacterium tuberculosis* antigen in cough", BMC Infectious Diseases, vol. 10, No. 1, Article 161, Jun. 8, 2010, 6 pages, https://doi.org/10.1186/1471-2334-10-161.
Moore et al., "Dry cotton or flocked respiratory swabs as a simple collection technique for the molecular detection of respiratory viruses using real-time NASBA", Journal of Virological Methods, vol. 153, Issue 2, Nov. 2008, pp. 84-89, https://doi.org/10.1016/j.jviromet.2008.08.001.
Morawska et al., "Size distribution and sites of origin of droplets expelled from the human respiratory tract during expiratory activities", Journal of Aerosol Science, vol. 40, Issue 3, Mar. 2009, pp. 256-269, https://doi.org/10.1016/j.jaerosci.2008.11.002.
Morsi et al., "An investigation of particle trajectories in two-phase flow systems", Journal of Fluid Mechanics, vol. 55, Issue 2, Sep. 26, 1972, pp. 193-208, https://doi.org/10.1017/S0022112072001806.
NIAID, "NIAID Biodefense Research Agenda for Category B and C Priority Pathogens", US Department of Health and Human Services, Jan. 2003, 66 pages.
NIAID, "NIAID Biodefense Research Agenda for Category B and C Priority Pathogens: Progress Report", US Department of Health and Human Services, Jun. 2004, 72 pages.

(56) References Cited

OTHER PUBLICATIONS

Nishiura et al., "Fever screening during the influenza (H1N1-2009) pandemic at Narita International Airport, Japan", BMC Infectious Diseases, May 3, 2011, vol. 11, Article 111, 11 pages, https://doi.org/10.1186/1471-2334-11-111.

Nolte et al., "Direct detection of *Mycobacterium tuberculosis* in sputum by polymerase chain reaction and DNA hybridization", Journal of Clinical Microbiology, vol. 31, No. 7, Jul. 1993, pp. 1777-1782.

Pai et al., "Point-of-Care Diagnostics for HIV and Tuberculosis: Landscape, Pipeline, and Unmet Needs", Discovery Medicine, vol. 13, No. 68, Jan. 18, 2012, pp. 35-45.

Papineni et al., "The Size Distribution of Droplets in the Exhaled Breath of Healthy Human Subjects", Journal of Aerosol Medicine, vol. 10, Issue 2, 1997, pp. 105-116, http://doi.org/10.1089/jam.1997.10.105.

Peiris et al., "Re-emergence of fatal human influenza A subtype H5N1 disease", The Lancet, vol. 363, Issue 9409, Feb. 21, 2004, pp. 617-619, https://doi.org/10.1016/S0140-6736(04)15595-5.

Perkins et al., "Facing the Crisis: Improving the Diagnosis of Tuberculosis in the HIV Era", The Journal of Infectious Diseases, 2007, vol. 196, Suppl 1, pp. S15-S27.

Petric et al., "Role of the Laboratory in Diagnosis of Influenza during Seasonal Epidemics and Potential Pandemics", The Journal of Infectious Diseases, The Journal of Infectious Diseases, vol. 194, Issue Supplement 2, Nov. 1, 2006, pp. S98-S110, https://doi.org/10.1086/507554.

Pfyffer et al., "Rapid detection of mycobacteria in clinical specimens by using the automated BACTEC 9000 MB system and comparison with radiometric and solid-culture systems", Journal of Clinical Microbiology, 1997, vol. 35, No. 9, pp. 2229-2234.

Phillips, "TB's revenge", Nature, vol. 493, Issue 7430, Jan. 2, 2013, pp. 14-16.

Piralla et al., "Segregation of Virulent Influenza A(H1N1) Variants in the Lower Respiratory Tract of Critically Ill Patients during the 2010-2011 Seasonal Epidemic", PLoS ONE, Dec. 14, 2011, vol. 6, Issue 12, Article e28332, 8 pages, https://doi.org/10.1371/journal.pone.0028332.

Sakundarno et al., "Insufficient quality of sputum submitted for tuberculosis diagnosis and associated factors, in Klaten district, Indonesia", BMC Pulmonary Medicine, May 8, 2009, vol. 9, No. 16, 11 pgs., doi:10.1186/1471-2466-9-16.

Schoch et al., "Diagnostic Yield of Sputum, Induced Sputum, and Bronchoscopy after Radiologic Tuberculosis Screening", Am. J. Respir. Crit. Care Med., 2007, vol. 175, pp. 80-86.

Scott II, "The Direct Medical Costs of Healthcare-Associated Infections in U.S. Hospitals and the Benefits of Prevention", Centers for Disease Control and Prevention, 2009, 16 pgs.

Sharma et al., "Multidrug-Resistant Tuberculosis: A Menace That Threatens to Destabilize Tuberculosis Control", Chest, vol. 130, No. 1, Jul. 2006, pp. 261-272.

Singh et al., "Pitfalls in Diagnosis of Pandemic (Novel) A/H1N1 2009 Influenza", Journal of Clinical Microbiology, Apr. 2010, vol. 48, No. 4, pp. 1501-1503, published online Feb. 17, 2010, doi: 10.1128/JCM.02483-09.

Sislian et al., "Bacterial aerosol neutralization by aerodynamic shocks using an impactor system: Experimental results for B. atropheus spores", Chemical Engineering Science, vol. 65, Issue 16, Aug. 15, 2010, pp. 4803-4815, https://doi.org/10.1016/j.ces.2010.05.035.

Sislian et al., "Bacterial aerosol neutralization by aerodynamic shocks using an impactor system: Experimental results for *E. coli* and analysis", Chemical Engineering Science, vol. 65, Issue 4, Feb. 15, 2010, pp. 1490-1502, https://doi.org/10.1016/j.ces.2009.10.029.

Sislian et al., "Bacterial aerosol neutralization by aerodynamic shocks using a novel impactor system: Design and computation", Chemical Engineering Science, vol. 64, Issue 9, May 1, 2009, pp. 1953-1967, https://doi.org/10.1016/j.ces.2009.01.021.

Tellier, "Review of Aerosol Transmission of Influenza A Virus", Emerging Infectious Diseases, Nov. 2006, vol. 12. No. 11, pp. 1657-1662, doi: 10.3201/eid1211.060426.

Teshima et al., "Biomechanical effects of shock waves on *Escherichia coli* and λphage DNA", Shock Waves, Apr. 1995, vol. 4, Issue 6, pp. 293-297.

Thompson et al., "Influenza-Associated Hospitalizations in the United States", The Journal of the American Medical Association, Sep. 15, 2004, vol. 292, No. 11, pp. 1333-1340, doi:10.1001/jama.292.11.1333.

Thompson et al., "Mortality Associated With Influenza and Respiratory Syncytial Virus in the United States", The Journal of the American Medical Association, Jan. 8, 2003, vol. 289, No. 2, pp. 179-186, doi:10.1001/jama.289.2.179.

Vitko et al., "Sensor Systems for Biological Agent Attacks: Protecting Buildings and Military Bases", The National Academies Press, 2005, 209 pgs.

Weber et al., "Comparison of Hospitalwide Surveillance and Targeted Intensive Care Unit Surveillance of Healthcare-Associated Infections", Infection Control and Hospital Epidemiology, 2007, vol. 28, No. 12, pp. 1361-1366.

WHO, "Diagnostics for tuberculosis, Global Demand and market potential", WHO, 2006, 205 pgs.

WHO, "Global Tuberculosis Control 2009, Epidemiology, Strategy, Financing", WHO Report 2009, 314 pgs.

Willeke et al., "Improved Aerosol Collection by Combined Impaction and Centrifugal Motion", Aerosol Science and Technology, vol. 28, Issue 5, 1998, pp. 439-456, https://doi.org/10.1080/02786829808965536.

World Health Organization, "Guidance for National Tuberculosis Programmes on the management of tuberculosis in children, Chapter 1 in the Series", Int. J. Tuberc. Lung Dis., 2006, vol. 10, No. 10, pp. 1091-1097.

Yeh et al., "Preferential Lower Respiratory Tract Infection in Swine-Origin 2009 A(H1N1) Influenza", Clinical Infectious Diseases, vol. 50, Issue 3, Feb. 1, 2010, pp. 391-394, https://doi.org/10.1086/64987.

Extended European Search Report for European Application No. 11804234.0, Search completed Apr. 26, 2017, dated May 8, 2017, 10 Pgs.

International Preliminary Report on Patentability for International Application PCT/US2011/042854, Report dated Jan. 8, 2013, 7 Pgs.

International Search Report and Written Opinion for International Application PCT/US2011/042854, report completed Nov. 1, 2011, dated Nov. 15, 2011, 8 Pgs.

"ANSYS FLUENT 12.0: Theory Guide", ANSYS, Inc., 2009 (presented in 6 parts).

"Estimates of Deaths Associated with Seasonal Influenza—United States, 1976-2007", Centers for Disease Control and Prevention, Morbidity and Mortality Weekly Report, vol. 59, No. 33, Aug. 27, 2010, pp. 1057-1089.

"Manual for the laboratory diagnosis and virological surveillance of influenza", WHO Global Influenza Surveillance Network, 2011, 153 pages.

Abouali et al., "A model for supersonic and hypersonic impactors for nanoparticles", Journal of Nanoparticle Research, 2005, vol. 7, No. 1, pp. 75-88.

Abu-Diab et al., "Comparison between Pernasal Flocked Swabs and Nasopharyngeal Aspirates for Detection of Common Respiratory Viruses in Samples from Children", Journal of clinical microbiology, vol. 46, No. 7, Jul. 2008, pp. 2414-2417, posted online May 14, 2008, doi: 10.1128/JCM.00369-08.

Andersen, "New sampler for the collection, sizing, and enumeration of viable airborne particles", Journal of Bacteriology, vol. 76, No. 5, Nov. 1958, pp. 471-484.

Bao et al., "Microfluidics-Based Lysis of Bacteria and Spores for Detection and Analysis", Principles of Bacterial Detection: Biosensors, Recognition Receptors and Microsystems, 2008, pp. 817-831.

Bardina et al., "Turbulence Modeling Validation, Testing, and Development", NASA Technical Memorandum 110446, Apr. 1997, 100 pages.

(56) References Cited

OTHER PUBLICATIONS

Biswas et al., "High-velocity inertial impactors", Environmental Science and Technology, vol. 18, No. 8, Aug. 1984, pp. 611-616, DOI: 10.1021/es00126a009.

Blakemore et al., "Evaluation of the Analytical Performance of the Xpert MTB/RIF Assay", Journal of Clinical Microbiology, vol. 48, No. 7, May 26, 2010, pp. 2495-2501, doi: 10.1128/JCM.00128-10.

Bogoch et al., "Diagnosis of influenza from lower respiratory tract sampling after negative upper respiratory tract sampling", Virulence, vol. 4, Issue 1, 2013, pp. 82-84, Published Online Nov. 7, 2012, https://doi.org/10.4161/viru.22466.

Cao et al., "Development of an improved methodology to detect infectious airborne influenza virus using the NIOSH bioaerosol sampler", Journal of Environmental Monitoring, vol. 13, Issue 12, 2011, pp. 3321-3328, DOI: 10.1039/C1EM10607D.

CDC, "Trends in Tuberculosis—United States, 2008", MMWR Weekly, Mar. 20, 2009, vol. 58, No. 10, pp. 249-253.

Chan et al., "Comparison of nasopharyngeal flocked swabs and aspirates for rapid diagnosis of respiratory viruses in children", Journal of Clinical Virology, May 2008, vol. 42, Issue 1, pp. 65-69, DOI 10.1016/j.jcv.2007.12.003.

Charrouf, "On the Fluid Dynamics of Virtual Impaction and the Design of a Slit Aerosol Sampler", PhD thesis, University of Maryland, College Park, May 2006, 187 pages.

Cheng et al., "Particle bounce in cascade impactors", Environmental Science & Technology, Nov. 1979, vol. 13, No. 11, pp. 1392-1396, DOI: 10.1021/es60159a017.

Clayden et al., "HIV, Hepatitis C Virus (HCV), and Tuberculosis (TB) Drugs, Diagnostics, Vaccines, and Preventive Technologies in Development", i-Base and Treatment Action Group, 2012 Pipeline Report, Jul. 2012, 267 pages (presented in 2 parts).

Conde et al., "Comparison of Sputum Induction with Fiberoptic Bronchoscopy in the Diagnosis of Tuberculosis", Am. J. Respir. Crit. Care Med., 2000, vol. 162, pp. 2238-2240.

Dawood et al., "Estimated global mortality associated with the first 12 months of 2009 pandemic influenza A H1N1 virus circulation: a modelling study", The Lancet Infectious Diseases, vol. 12, Issue 9, Sep. 2012, pp. 687-695, https://doi.org/10.1016/S1473-3099(12)70121-4.

De Vos et al., "Direct detection and identification of Pseudomonas aeruginosa in clinical samples such as skin biopsy specimens and expectorations by multiplex PCR based on two outer membrane lipoprotein genes, oprI and oprL", Journal of Clinical Microbiology, vol. 35, No. 6, Jun. 1997, pp. 1295-1299.

Dehbi, "A CFD model for particle dispersion in turbulent boundary layer flows", Nuclear Engineering and Design, vol. 238, Issue 3, Mar. 2008, pp. 707-715, https://doi.org/10.1016/j.nucengdes.2007.02.055.

Dimaio et al., "Comparison of Xpert Flu rapid nucleic acid testing with rapid antigen testing for the diagnosis of influenza A and B", Journal of Virological Methods, vol. 186, Issues 1-2, Dec. 2012, pp. 137-140, https://doi.org/10.1016/j.jviromet.2012.07.023.

Dunlap et al., "Diagnostic Standards and Classification of Tuberculosis in Adults and Children", American Journal of Respiratory and Critical Care Medicine, 2000, vol. 161, No. 4, pp. 1376-1395.

Dwyer, "Matchmaking and McNemar in the comparison of diagnostic modalities", Radiology, vol. 178, Issue 2, Feb. 1991, pp. 328-330, https://doi.org/10.1148/radiology.178.2.1987587.

Fabian et al., "Influenza Virus in Human Exhaled Breath: An Observational Study", PLoS ONE, vol. 3, Issue 7, Article e2691, Jul. 16, 2008, 6 pages, https://doi.org/10.1371/journal.pone.0002691.

Giannella et al., "Prolonged viral shedding in pandemic influenza A(H1N1): clinical significance and viral load analysis in hospitalized patients", Clinical Microbiology and Infection, vol. 17, Issue 8, Aug. 2011, pp. 1160-1165, Oct. 14, 2010 https://doi.org/10.1111/j.1469-0691.2010.03399.x.

Gupta et al., "Flow dynamics and characterization of a cough", Indoor Air, 2009, vol. 19, pp. 517-525.

Gupta et al., "Transport of expiratory droplets in an aircraft cabin", Indoor Air, vol. 21, Issue 1, Feb. 2011, pp. 3-11, First published: Jan. 5, 2011, https://doi.org/10.1111/j.1600-0668.2010.00676.x.

Hawass, "Comparing the sensitivities and specificities of two diagnostic procedures performed on the same group of patients", The British Journal of Radiology, vol. 70, Issue 832, 1997, pp. 360-366, https://doi.org/10.1259/bjr.70.832.9166071.

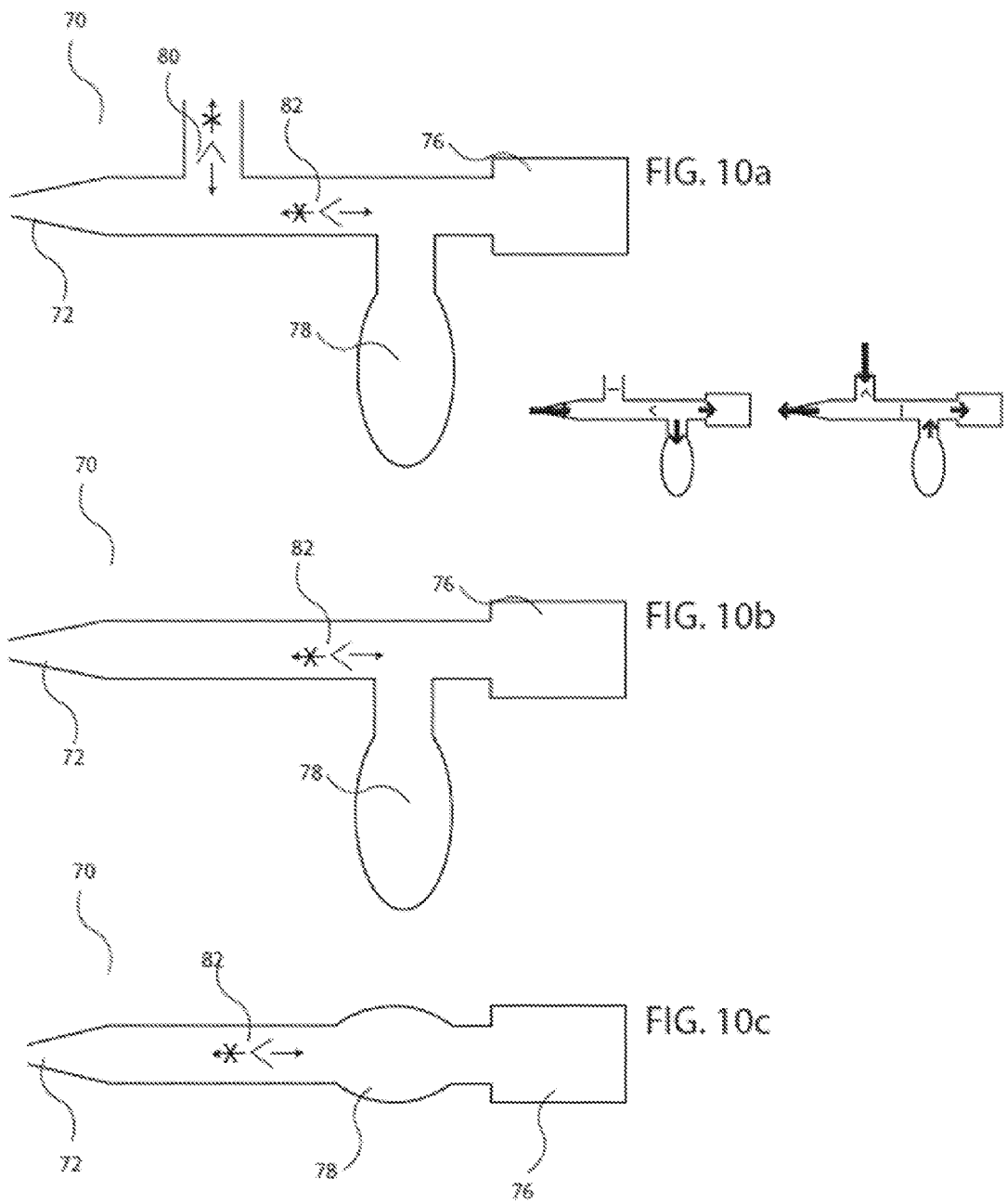

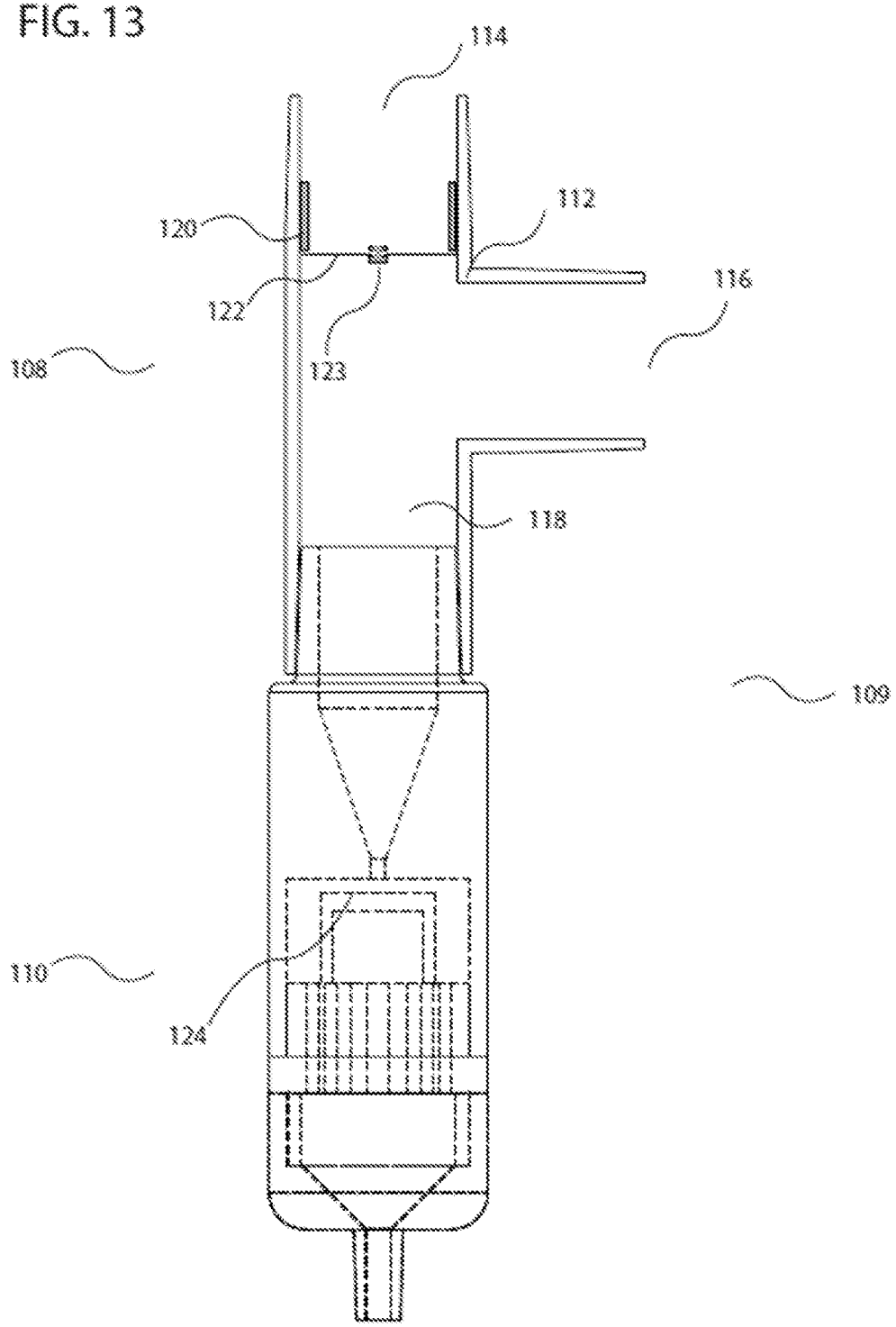

SYSTEM FOR BREATH SAMPLE COLLECTION AND ANALYSIS

STATEMENT REGARDING FEDERALLY SPONSORED RESEARCH OR DEVELOPMENT

This invention was made with Governmental support under Grant No. IIP-1113148 awarded by the National Science Foundation and Grant No. 1R43AI102418-01 awarded by the National Institutes of Health. The Government has certain rights in the invention.

FIELD OF THE INVENTION

The current invention is directed to a system for collecting and analyzing bacteria or biological particles; and more particularly to a system comprising an aerosol collection system for airborne bacterial or biological particle detection that can be used to prepare a sample for diagnosis or directly diagnose a sample for bacterial infection from the environment or from a patient, such as, for example, tuberculosis.

BACKGROUND OF THE INVENTION

Collecting a quality sample for the diagnosis of respiratory diseases presents multiple challenges. The challenges are nuanced between the different disease states but common themes emerge. As an example tuberculosis, influenza and pneumonia are three diseases that each represent particular diagnosis challenges.

Active Tuberculosis (TB) causes approximately 2 million annual deaths, making it the second leading cause of death from infectious diseases worldwide. An estimated 9.3 million people worldwide develop TB every year, of which ~4.4 million are undiagnosed. TB also poses a significant bioterrorism threat. *M. tuberculosis* is classified as a NIAID Category C Priority Pathogen and is transmitted primarily through airborne droplets (as few as 2 droplets can cause TB infection). Multiple-drug resistant strains further complicate TB diagnosis and treatment, boosting its threat as a bioterrorism agent. When diagnosed properly TB can be treated. Currently, sputum expectorate is the most common sampling method used for TB diagnosis. Diagnostics that rely on sputum samples suffer from disadvantages associated with sputum collection. Sputum is difficult to collect from some patients (children and elderly), and is unattainable from expectoration deficient patients (~20% of patients). In these cases, procedures such as sputum induction and gastric aspiration are required; all of which are difficult to administer and risky as they expose healthcare providers to contagious specimens. In other cases, bronchoscopy with bronchoalveolar lavage (BAL) is performed. This procedure is costly, requires a physician, and can cause complications associated with conscious sedation. In the case of a bioterrorist attack, these methods can become prohibitive. When sputum samples are attainable, contamination by oropharyngeal flora, saliva, mucus, and cell debris negatively affects the sensitivity and specificity of diagnostics. Even uncontaminated and undiluted sputum can inherently have low concentrations of *M. tuberculosis* in patients infected with TB.

Pneumonia is the leading cause of death among infectious diseases in the United States where ~1.1M people are hospitalized and ~50,000 die each year. Pneumonia is an infection of the lower respiratory tract (LRT) and is typically caused by viruses and/or bacteria. A major challenge in diagnosing pneumonia is obtaining a quality sample namely because etiologic agents of pneumonia often colonize the upper respiratory tract (URT) of healthy subjects without causing LRT infection. If a diagnostic sample contains URT contaminants, the sample is discarded (low diagnostic yield) or a false etiologic agent may be identified (low specificity). Sputum or bronchoalveolar lavage (BAL) are the most common samples used to identify the etiologic agent of pneumonia. However, both samples suffer significant limitations. Sputum cannot be produced by all patients, particularly in children under the age of 5. Even with the help of induction, sputum is unobtainable in an estimated 40% of pneumonia patients. When collected, sputum samples suffer from contamination of the URT flora, and up to 50% of the samples are discarded. Although BAL provides a higher quality sample for diagnostic analysis, it is invasive, requires sedation, and is therefore only recommended in high-risk patients. As a result, community-acquired pneumonia (CAP) is treated using a broad-spectrum antibiotic regimen in the absence of a diagnostic sample. Since the epidemiology of hospital-acquired pneumonia (HAP) is vastly different than CAP, HAP cannot be treated with the same empirical antibiotic regimen; rather, the identification of an etiology prior to treatment is necessary. In HAP, a BAL is the recommended sample for diagnosis. To obtain an uncompromised sample at minimal risk to patients and encourage antimicrobial stewardship in clinical practice, new methods of non-invasive lower tract sample collection are needed. Better sample collection would serve to improve the <10% yield in the diagnosis of an etiologic agent in CAP and replace invasive procedures in HAP.

Seasonal influenza is a threat to global public health causing 3-5M cases of severe illness and 250,000 deaths each year. Pandemic influenza arises when a new strain, for which little prior immunity exists, begins circulating in the human population. Most recently, the 2009 A(H1N1) swine flu pandemic caused an additional 280,000 deaths. Alarmingly, certain influenza strains, such as the A(H1N1) swine flu and the A(H5N1) avian flu, have an increased propensity to infect the lower respiratory tract and cause severe illness. Influenza diagnosis is typically performed on samples collected from the throat and nasal cavities of the upper respiratory tract, using nasopharyngeal (NP) swabs. However, only invasive procedures can collect samples for the proper diagnosis of lower respiratory tract influenza. In particular, during the recent A(H1N1) pandemic, many influenza cases were diagnosed as negative from NP swab samples but were positive from lower respiratory tract samples. These findings highlight the need to analyze lower respiratory tract samples from patients with severe influenza-like illness. Administration of antiviral therapies can be applied more appropriately, thereby improving patient treatment. Finally, influenza surveillance data collected exclusively from upper respiratory tract samples may miss emerging strains that preferentially target the lower respiratory tract. Current methods of obtaining samples from the lower respiratory tract, such as transtracheal aspiration, bronchoalveolar lavage, and lung biopsy are highly invasive.

Other disease states can also benefit from improvements in sample collection methodologies. These can include but are not limited to Non-tuberculosis mycobacterial infection and respiratory syncytial virus. However, the challenges represented by just these three diseases demonstrate that the field of diagnostics would benefit improved sample collection methodologies.

SUMMARY OF THE INVENTION

In many embodiments the disclosure is directed to systems for collecting and analyzing bacteria or biological particles, and to prepare a sample for diagnosis or directly diagnose a sample for bacterial infection from the environment or from a patient, such as, for example, tuberculosis.

In some embodiments, the invention is directed to a biological sample collector system including:
- a pre-collection assembly configured to engage with a patient such that the entirety of the outflow of breath from the patient including any biological particulates contained therein is captured within the collector system;
- a sample reservoir defining a volume having therein a sample medium for entraining the target biological particulates in the sample medium to form a sample analyte suitable for diagnostic analysis;
- a collector in fluid communication between the pre-collection assembly and the sample reservoir, and having at its terminating end a fluid focusing nozzle, the collector being configured to select said biological particulates of greater than a target size from said outflow of breath and direct said target biological particulates into said sample reservoir such that efficient transfer of the target biological particulates into the sample medium is obtained; and
- wherein at least a portion of the outflow of breath flows through said pre-collection assembly and into said collector in any single breath, and wherein the remainder of the outflow of breath is temporarily stored within said pre-collection assembly.

In other embodiments the angle formed between the entry of the fluid focusing nozzle and the collector upstream of said nozzle is configured such that recirculation zones are prevented from forming in the nozzle entrance, wherein the length of the nozzle is configured to prevent the biological particulates from reaching their terminal velocity, wherein the diameter of the nozzle is configured to reduce particle bounce and increase collection at a specified flow rate, and wherein the ratio of the length of the nozzle to the diameter of the nozzle is configured such that the biological particulates do not intercept the walls of the nozzle.

In still other embodiments the sample reservoir is incorporated into a cartridge module in fluid connection with the collector, the cartridge module being removable from said collector system and being configured to cooperatively engage with an input of a diagnostic analyzer. In some such embodiments the cartridge module containing the sample reservoir comprises a self-sealing mechanism configured to isolate the sample medium from the external atmosphere. In other such embodiments the portion of the cartridge module containing the sample reservoir includes a mechanism for ejecting the sample medium into the input of the diagnostic analyzer.

In yet other embodiments the sample medium contained within the sample reservoir takes a form selected from the group consisting of a tablet, a pelletized salt, a liquid, a film, and a gel.

In still yet other embodiments the entrance to the sample reservoir is disposed opposite the fluid focusing nozzle. In some such embodiments an exposed surface of the sample medium contained within the sample reservoir is dimensioned to be on the order of the diameter of the nozzle. In other such embodiments the sample medium is a liquid and the sample reservoir further comprises an airspace between the end of the nozzle and the exposed surface of sample medium, and wherein the cross-section of the airspace, the cross-section of the nozzle and the distance between the end of the nozzle and the exposed surface of the sample medium are configured such that the velocity of the outflow at the exposed surface of the sample medium is less than 20 m/s.

In still yet other embodiments the ratio of the distance from the end of the nozzle and the exposed surface of the sample medium and the nozzle diameter is greater or equal to 1.2 and less than or equal to 1.6.

In still yet other embodiments the angle formed between the entry of the fluid focusing nozzle and the collector upstream of said nozzle is less than 30° such that recirculation zones are prevented from forming in the nozzle entrance.

In still yet other embodiments the ratio of the length of the nozzle to the diameter of the nozzle is less than 2.25.

In still yet other embodiments the nozzle diameter is configured such that the velocity of the biological particulates at the surface of the sample medium multiplied by the particle diameter is less than 50 to control biological particulate bounce against the surface of the sample medium such that the collection efficiency of the particle size of interest is greater than 0.9.

In still yet other embodiments the collector has a specified flow capacity, and wherein the pre-collector assembly further comprises a temporary storage volume configured to capture any portion of the outflow of breath from the patient that exceeds the flow capacity of the collector. In some such embodiments the temporary storage includes a one-way valve mechanism whereby the breath captured in the temporary storage volume is prevented from being inhaled by the patient and releases the captured breath into the collector during an inhalation by the patient. In other such embodiments the one-way valve is triggered by one of either an automated mechanism or manually by the patient. In still other such embodiments the pre-collector assembly further comprises a second one-way valve that allows an inhalation of breath by the patient through the pre-collector assembly. In yet other such embodiments the temporary storage volume is formed of an elastic material, such that the temporary storage volume stores at least a portion of both the volume of the outflow of breath and the work of the outflow of breath as potential energy, and wherein the potential energy may be converted to a kinetic flow by releasing said stored portion of the outflow of breath into the collection system.

In still yet other embodiments the pre-collector assembly further comprises a filter mechanism for filtering out biological particulates of greater than a target size from said target biological particulates. In some such embodiments the filter mechanism comprises a one-way valve configured to bend during exhalation by a patient such that particulates greater than the target size impact the valve and are prevented from entering the collector.

In still yet other embodiments the collector further comprises an aerodynamic impactor having first and second ends and defining a fluid path therein, and wherein the aerodynamic impactor applies an inertial deceleration force to the gaseous sample, and wherein the magnitude of the inertial force can be varied such that at a low inertial force any biological particulates within the sample are passed through the impactor intact and that at an inertial force above a threshold any biological particulates within the sample are lysed to release the internal components thereof. In some such embodiments the internal components of the target biological particulates contain DNA.

In still yet other embodiments the system further includes a positive control configured to provide an indication that a sufficient volume of the outbreath of the patient has been collected. In some such embodiments the positive control is selected from the group consisting of an indicator for a signature biological material and a physical measurement of the outflow of breath from the patient.

In still yet other embodiments the pre-collector assembly further comprises a humidity control system configured to prevent particle growth.

Additional embodiments and features are set forth in part in the description that follows, and in part will become apparent to those skilled in the art upon examination of the specification or may be learned by the practice of the disclosed subject matter. A further understanding of the nature and advantages of the present disclosure may be realized by reference to the remaining portions of the specification and the drawings, which forms a part of this disclosure.

BRIEF DESCRIPTION OF THE DRAWINGS

The description will be more fully understood with reference to the following figures and data graphs, which are presented as various embodiments of the disclosure and should not be construed as a complete recitation of the scope of the disclosure.

FIGS. 10a to 10c provide schematics of pre-collector assemblies in accordance with embodiments of the invention.

FIG. 13 provides a schematic of a sample collection system in accordance with embodiments of the invention.

DETAILED DESCRIPTION OF THE INVENTION

Figure 1:
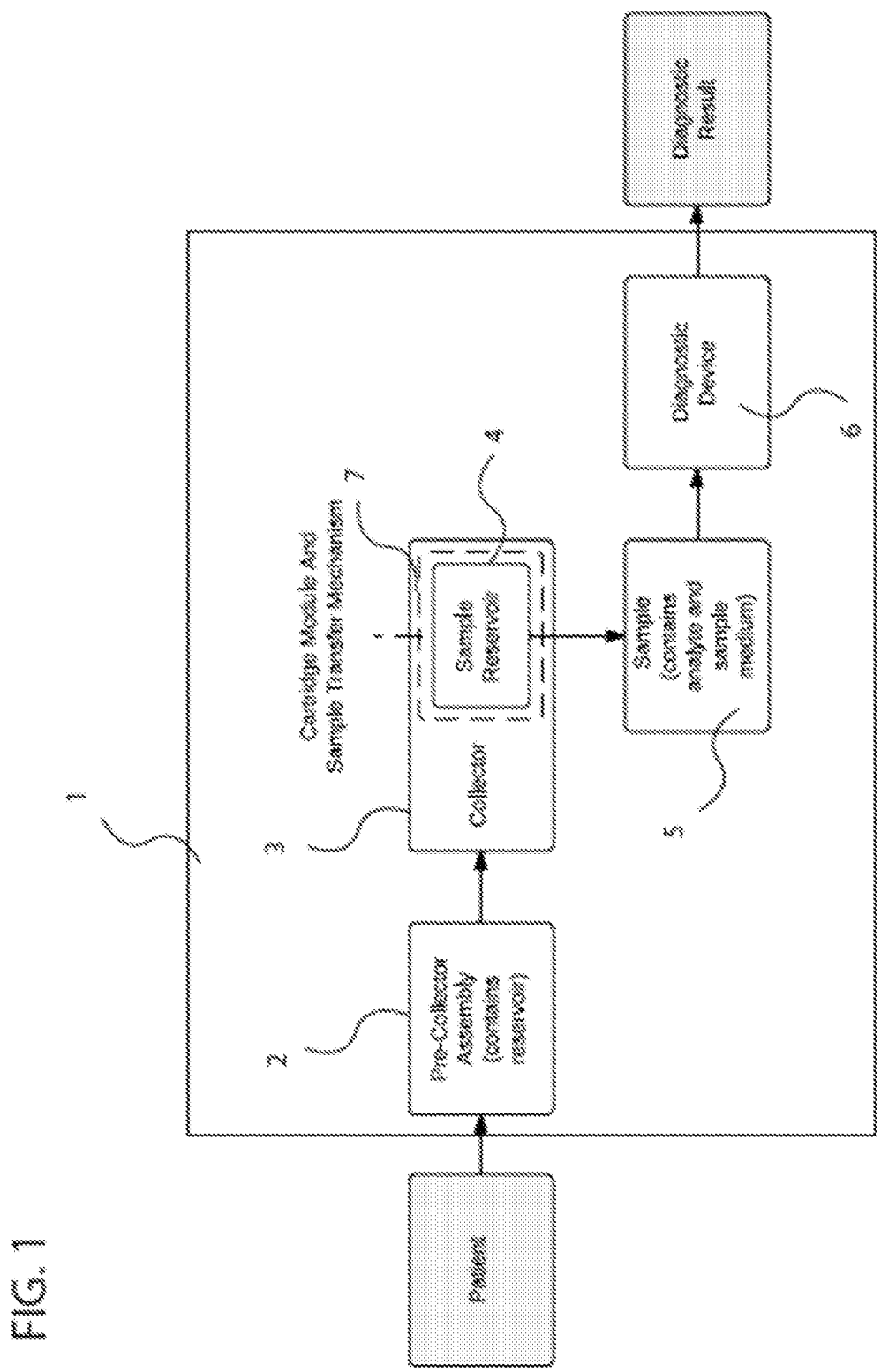
FIG. 1 provides a schematic of an embodiment of a sample collection and analysis system in accordance with embodiments of the invention.

Turning now to the drawings, systems and methods for collecting samples from a patient for diagnosis are illustrated. In many embodiments, the sample collection and analysis system concentrates particles emanating from a patient's cough, sneeze, or breathe in a sample for the diagnosis of a respiratory tract infection or other ailment of the patient. In some such embodiments (as shown schematically in FIG. 1) the sample collection and analysis system (1) has a pre-collection assembly (that is patient interface 2), a collector (3) in fluid communication between the pre-collection assembly and a sample reservoir (4) that function in combination to: efficiently capture the volume of air expelled from the subject, direct the expelled air towards a sample reservoir, and separate the desired particle sizes from the expelled air into the sample reservoir.

In many embodiments, expelled particles collected in the sample reservoir are the source of analyte that produces a signal in the transducer of a diagnostic device sensor. In such embodiments, this analyte can be any one or more of liquid droplets containing organic, inorganic or biological molecules that provide a signature of the illness; liquid droplets that contain fragments or intact live or dead bacterial cells, viruses, or cells originating from the subject; and dry fragments or intact live or dead bacterial cells, viruses, or cells originating from the subject. For the purposes of this disclosure, these particles (or analytes) along with the material that makes up the collection reservoir are referred to as the sample (5), which may be transferred to a diagnostic device (6) to produce a diagnostic result of the ailment in question.

The embodiments that follow will provide for the above function and can be used in any combination in the sample collection system.

Although specific embodiments of elements of the sample collection and analysis system that provide for the above function will be described in detail below, it should be understood that these embodiments and elements may be used in any combination with any of a variety of such systems as appropriate to the requirements of a specific application.

Cartridge Module and Sample Transfer Mechanism

In many embodiments the sample collection and analysis system is configured to be used as a fully integrated patient-to-diagnosis device. Such operation requires a seamless transfer of sample from the sample collection device to an appropriate diagnostic device. To accomplish this a sample is collected in a sample reservoir. As will be discussed in greater detail, below, the sample reservoir medium can take many forms. Regardless of the sample medium, in embodiments the sample can be transferred to a diagnostic device either continuously or in batch. For continuous transfer a microfluidic system would be integrated whereby the collected material is directly transferred to the diagnostic device, which can either detect the material in batch or real-time, as described previously in U.S Pat. Pub. No. 2013/0217029, the disclosure of which is incorporated herein by reference. However, in batch transfer embodiments a cartridge module (7) may be incorporated into the sample collection system. In many embodiments, the module includes a mechanism that facilitates the transfer of sample. In such embodiments the cartridge module may include one or more of the following design elements:

- an easily removable module that is an integrated portion of the sample collection system;
- labeled, such as by barcoding, to easily associate the sample with the patient;
- containing a sample reservoir, which in turn is configured to contain the sample;
- compatible and directly cooperative with a diagnostic device, for example, a cartridge module may engage with and dispense a sample into the diagnostic device such as a Cepheid Xpert™ or a BioFire FilmArray™; and
- is cooperative with the sample gathering geometries described below.

Figure 2:
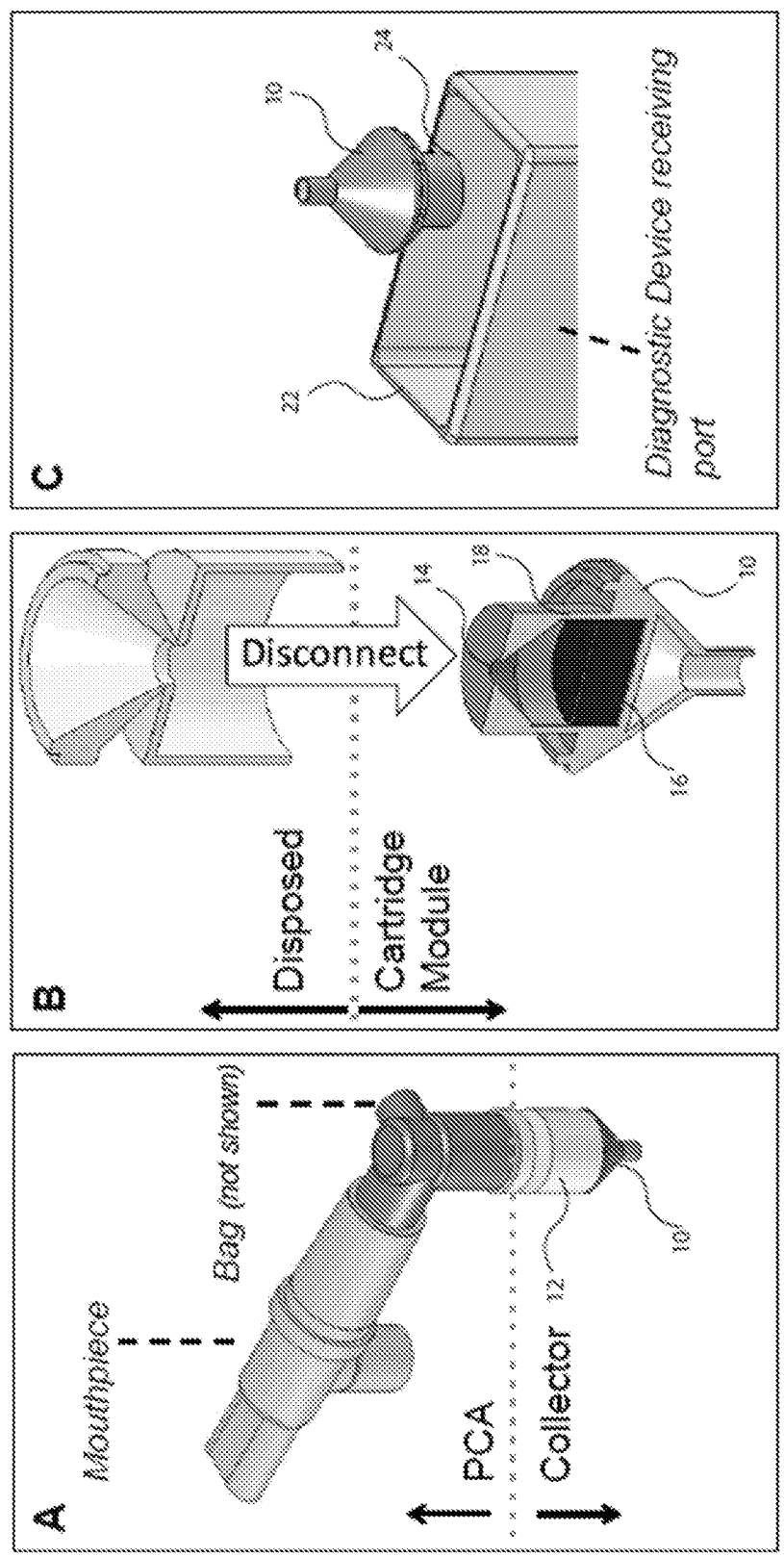
FIGS. 2a to 2c provide schematics of embodiments of a cartridge module and mechanism of sample transfer in accordance with embodiments of the invention.

In many such embodiments, the mechanism of sample transfer is integrated into the cartridge module, such mechanism being mechanical, electrical, or any mechanism or combination. Such a removal mechanism may include one or more of the following design elements:

- A removal means that includes one or both of a twist-off, snap-off, or other mechanism.
- A self-sealing cartridge module that seals the sample reservoir once removed from the collection system, thus preventing the sample, which might contain biohazards, from being exposed to the external environment or exposing personnel to such biohazards, and also preventing contamination of the sample by external environmental elements.
- In many embodiments, the cartridge module also acts as a storage vehicle. In such embodiments the cartridge module preserves the sample reservoir before collection and before transferring (i.e. after collection) the sample to the diagnostic device. Therefore, the cartridge module is configured to withstand a wide temperature range to maintain the integrity of the sample reservoir and the sample it contains (low temperatures for post-collection storage and high temperatures for on shelf storage pre-collection).
- In still other embodiments (as shown in FIG. 2c) the dispensing mechanism either allows integration of the cartridge module with a specific diagnostic device, transfer of the sample into a standard use tube or vial after which a standard transfer pipette is used, or any other receptacle. In such embodiments, a mechanism is built in to the cartridge module to actively force the sample in the sample reservoir out whereby there is a seal created to isolate the transfer from the outside environment. In some such embodiments, where the sample reservoir medium is a tablet (as described below), a device (such as a clicker) in the cartridge module mechanically ejects the tablet into the diagnostic device (such as a tube), which could contain water or other buffers where the tablet containing the collected analyte may be dissolved and ready for detection. In another embodiment, where the sample reservoir medium is a buffer (as described below), the cartridge module can contain a mechanism (not shown), such as a plunger of the type used in syringes, whereby a piston drives the analyte-containing liquid to the receptacle.

The operation of certain embodiments of a cartridge module incorporating the features above are describe in relation to FIGS. 2a to 2c. In such embodiments, the sample collection system (12) comes prepackaged with all parts including the cartridge module (10), as shown in FIG. 2a. After a sample is collected from the patient, the cartridge module is disconnected, as shown in FIG. 2b. In such embodiments, the cartridge module (10) includes a sample reservoir (16). In the collector, the particles generated by the patient flow through a nozzle. The mechanism of creating flow through collector will be described in greater detail below. In the collector, the sample reservoir is placed perpendicular to the flow exiting the nozzle, which causes the flow to bend. The particles cannot follow the change in direction and are directed towards the sample reservoir where they are collected. (For a full description of the nozzle and its placement in relation to the collector and sample region see, for example, U.S Pat. Pub. No. 2013/0217029, cited above.) In this embodiment the sample reservoir is a cavity facing the nozzle (20) that focuses the stream of the incoming outflow of breath, and that contains a liquid buffer (16) as the sample reservoir medium. The analyte is collected in the medium, which becomes the analysis sample. Once the cartridge module (10) is disconnected, the orifice (14) in the sample reservoir (16) shuts (not shown) using a mechanism, in one embodiment this mechanism can be a spring, as shown in FIG. 2b. The cartridge module can then be used as a storage device that preserves the sample. The cartridge module then integrates with a diagnostic device (22) receiving port (24) creating a seal, as shown in FIG. 2c. The cartridge module then can be operated to dispense the sample through a mechanism, in one embodiment this mechanism can be a plunger (not shown) as well, that also forces the orifice to open and eject the analyte.

Sample Reservoir Design

Figure 3:
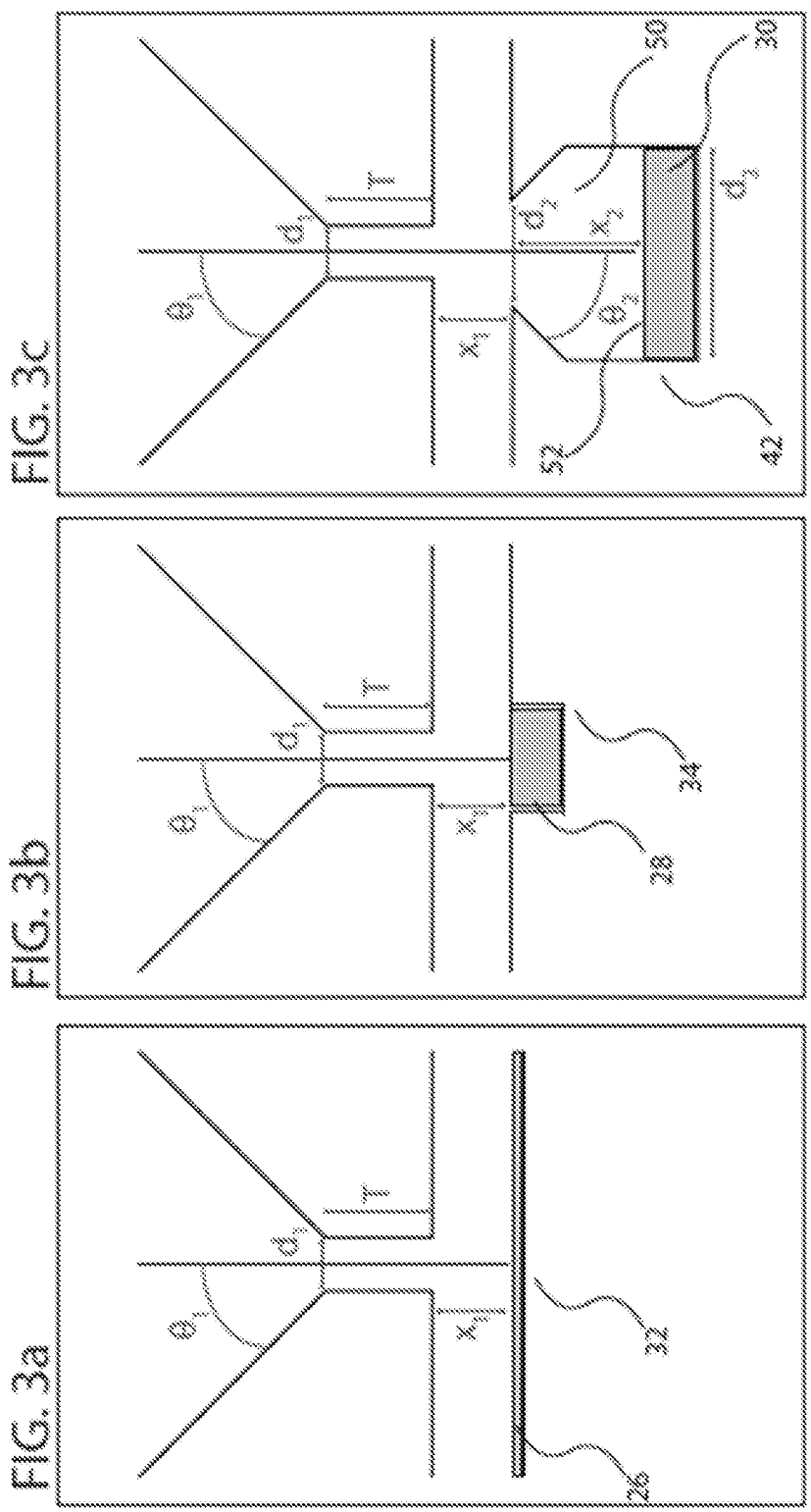
FIGS. 3a to 3c provide schematics of sample reservoirs shown in a cross section of a collector in accordance with embodiments of the invention.

In embodiments, the sample reservoir is defined as the medium that accepts the separated particles from the patient's cough, sneeze or breath and concentrates them. Therefore, in embodiments the material contained within the reservoir is small enough to allow for the sample to be less than 2 mL prior to being fed into the diagnostic device. The dimensions of the sample reservoir medium (26, 28, 30 in FIGS. 3a to 3c) are on the order of the nozzle diameter (d1). The sample reservoir itself (32, 34, 36) is located opposite the nozzle (38, 40, 42), and can be of varying geometries some of which are shown in FIGS. 3a to 3c. Both of the geometries shown in FIGS. 3a and 3b have similar collection characteristics in that the air exiting the nozzle encounters a flat plate.

Figure 4:
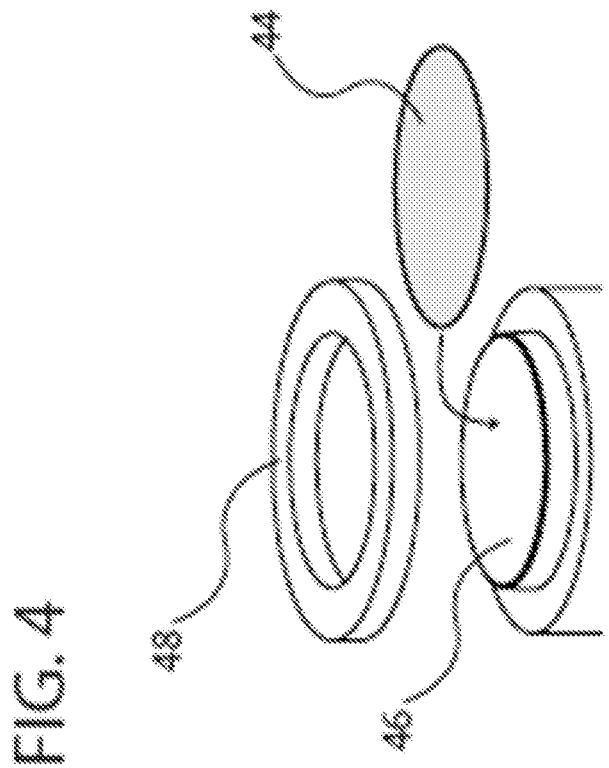
FIG. 4 provides a schematic of a sample reservoir in a polycarbonate surface fixed at its edges on the flat surface using a tapered ring in accordance with embodiments of the invention.
Figure 5:
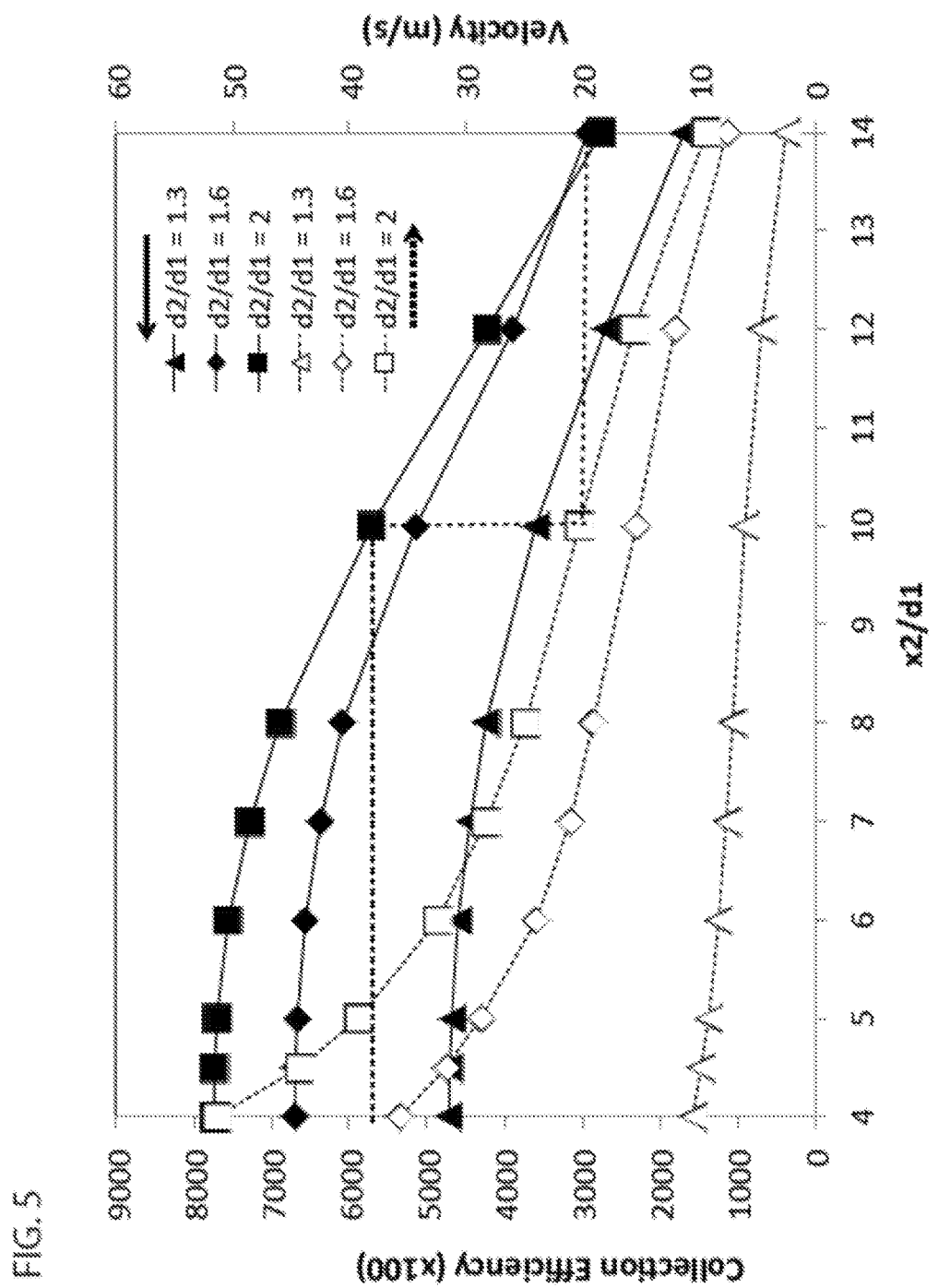
FIG. 5 provides a data graph obtained from computational fluid dynamics (CFD) simulations showing the relationship that d2 and x2 have in relationship to collection efficiency and velocity at the sample reservoir surface in accordance with embodiments of the invention.
Figure 6:
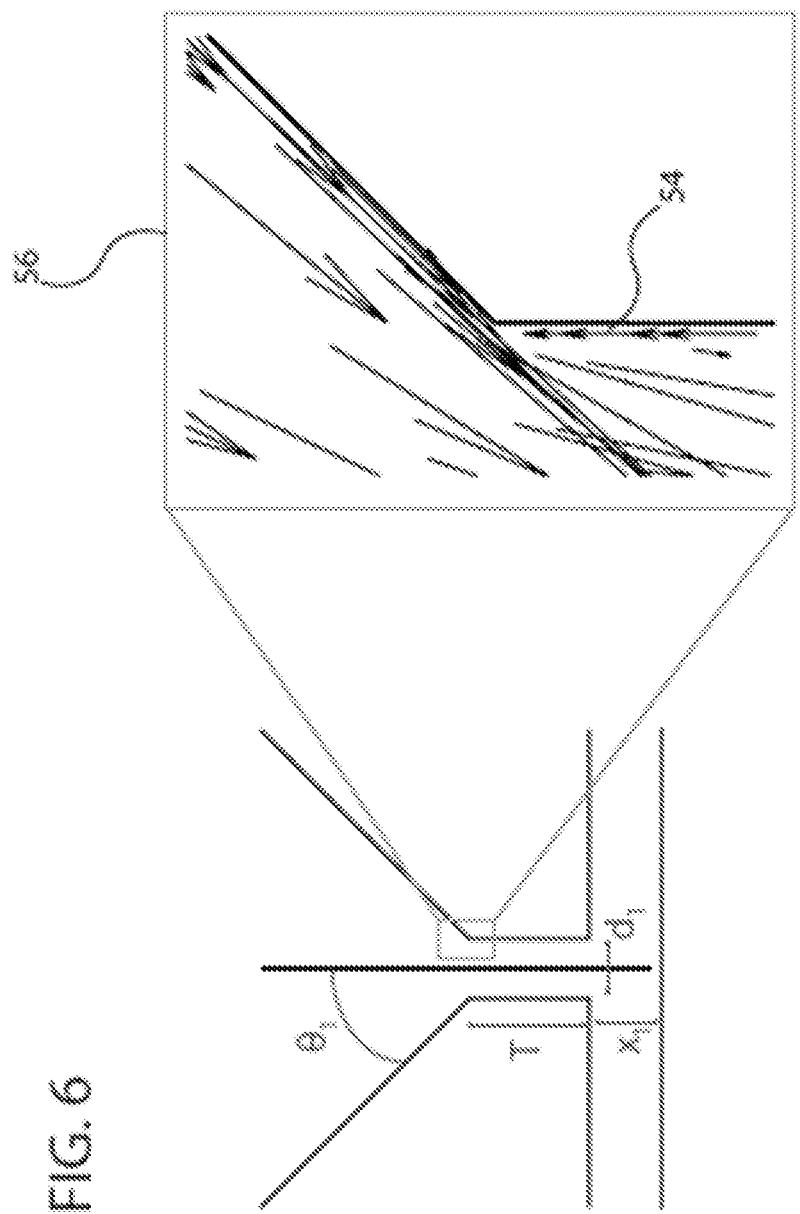
FIG. 6 provides a schematic of a cross section of a collector and CFD data driven vectors of velocities at the entrance of the collector nozzle in accordance with embodiments of the invention.
Figure 7:
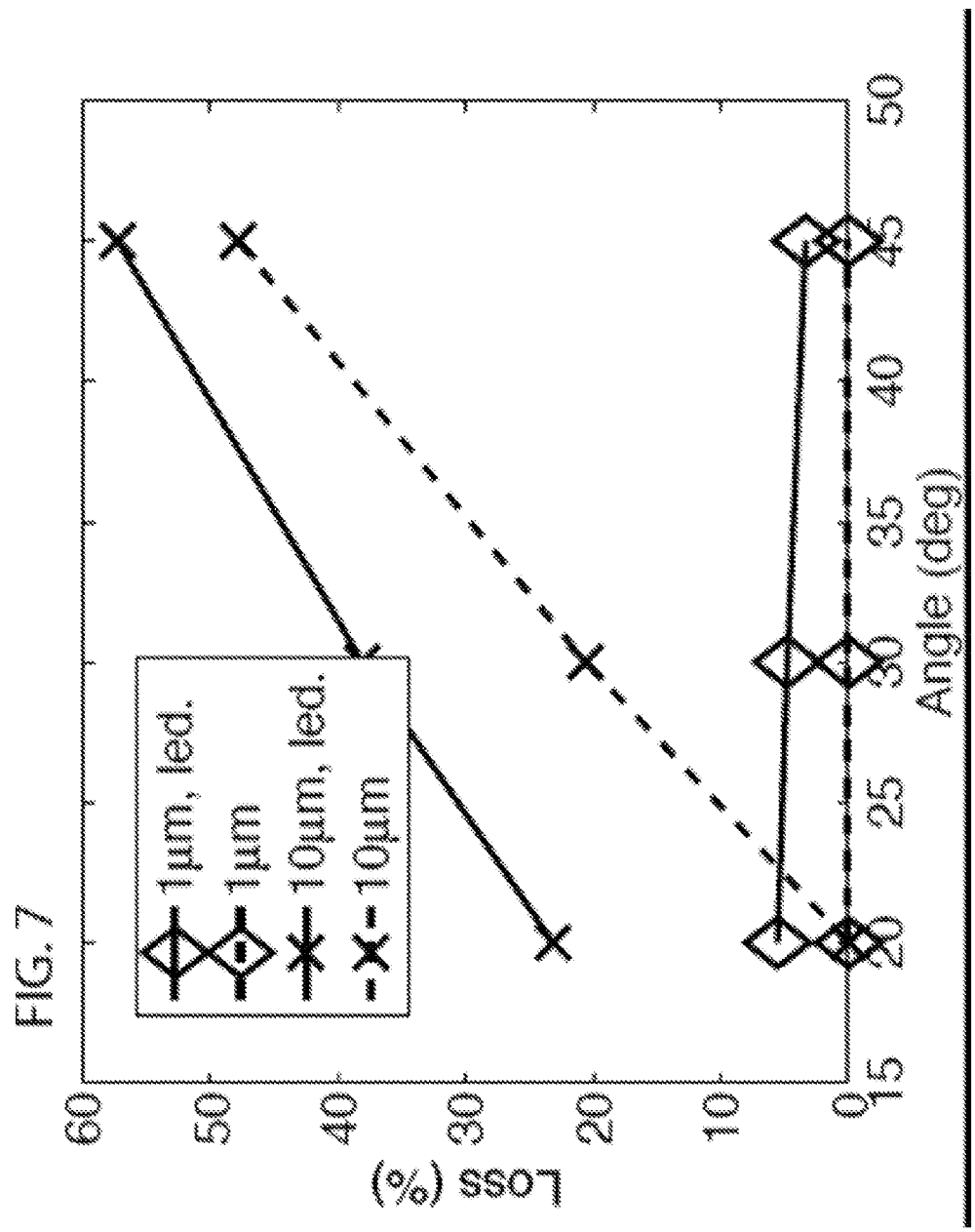
FIG. 7 provides a data graph obtained from CFD simulations showing the relationship between nozzle angle and wall losses in accordance with embodiments of the invention.
Figure 8A:
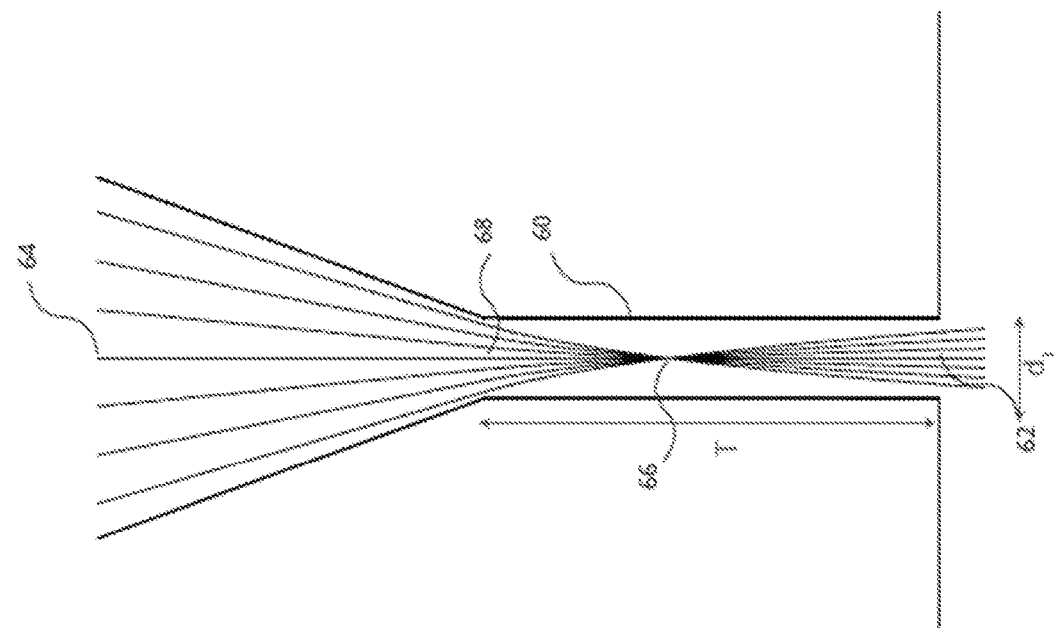
FIGS. 8a and 8b provide schematics of the cross section of collector embodiments with different nozzle throat lengths overlaid on the schematic is CFD data driven particle tracks in accordance with embodiments of the invention.
Figure 8B:
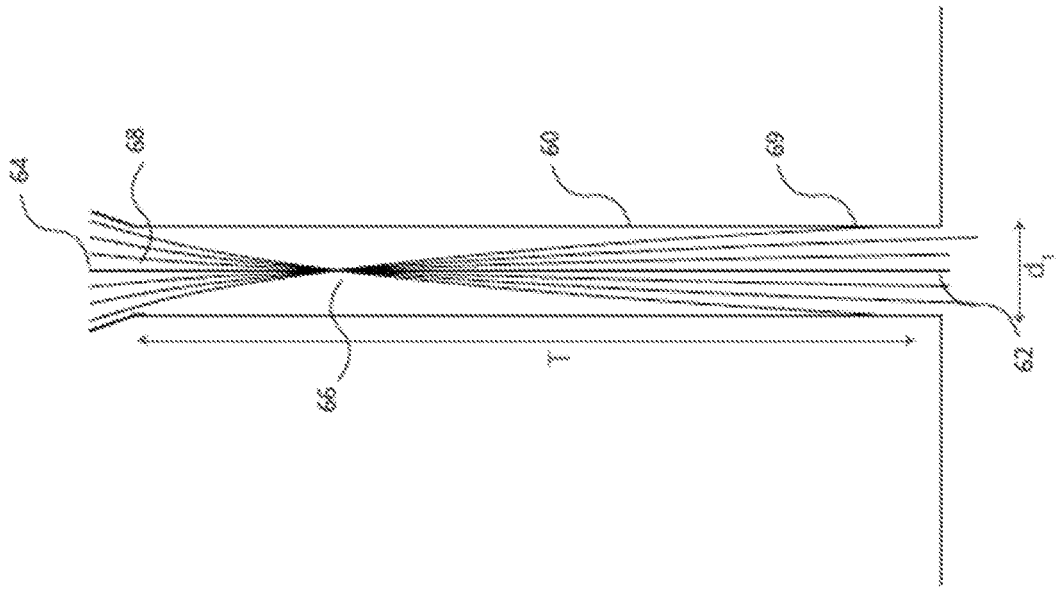

The sample reservoir medium (26, 28, 30) in which the particles are collected can vary—some being suited for only specific geometries and not others. The common factor in all these sample reservoir media is that they have to be compatible with the downstream diagnostic detection methodology. For instance, if the method used is polymerase chain reaction (PCR) amplification to detect the analyte, then media that do not inhibit the PCR have to be used. For example, the geometry in FIG. 3a is suited for use with a flat solid material or films (26). One embodiment of this design is the use of a polycarbonate film (44), which is fixed at its edges on a flat surface (46) using a tapered ring (48) (see FIG. 4). The analyte lies on the surface of the flat solid material and can be transferred to liquid by placing the film in an extraction liquid. Extraction of intact cells can be performed using sonication for 1 min or DNA can be extracted using DNA extraction kits.

Other embodiments, as shown in the geometry provided in FIG. 3b, are suited for a thicker solid material that cannot be obtained in a film. For example different salts are not stable as a film. Accordingly, the material of choice in these cases has to be a material that dissolves. In one embodiment, the salts of choice are pelletized and inserted in the sample reservoir (34). The analyte is collected on the surface and after the collection the analyte is extracted into liquid by dissolution. In another embodiment, a polyethylene glycol (PEG) gel or viscous liquid is placed in the sample reservoir. PEG molecules of different lengths are water-soluble at different water content levels. This property can then be used to control the dissolution of the PEG gel that contains the analyte.

Figures 9A, 9B:
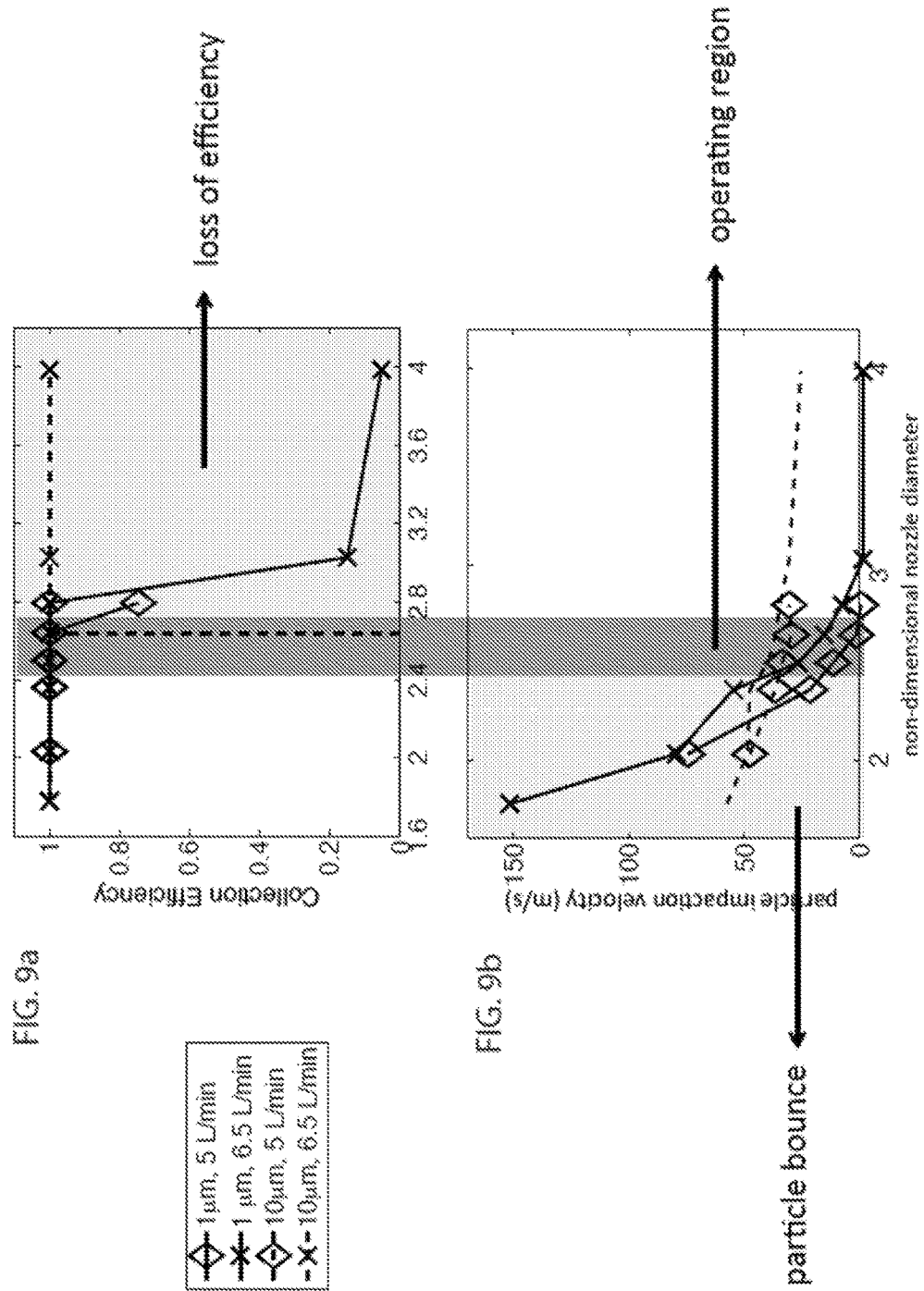
FIGS. 9a and 9b provide data graphs showing the relationship of nozzle diameter (d1) to collection efficiency and impaction velocity in accordance with embodiments of the invention.

In the embodiment shown schematically in FIG. 3c, all the materials discussed with respect to FIGS. 3a and 3b can be used. In addition, liquid collection is possible, as described in U.S Pat. Pub. No. 2013/0217029, cited above. In such embodiments a cavity (50) is disposed in relation to the sample reservoir allowing the airflow to decelerate prior to contacting the collection surface (52) (liquid, film, or solid) of the sample reservoir. This prevents the airflow from carrying droplets from the liquid surface and eventually depleting the sample (30). However, careful consideration has to be taken in terms of properly designing the cavity (50). In some embodiments, the opening to the cavity (50) has a diameter d2, and the liquid is placed at a distance x2 from the opening. These two parameters have to be controlled in relation to the nozzle diameter d1.

In determining the appropriate parameters, two competing phenomena have to be balanced: 1) the collection efficiency of particles (that is, how many particles penetrate to the liquid), and 2) the velocity of air at the liquid surface (that is, will the air will carry liquid as it contacts the surface). In order to prevent the air from depleting the liquid, the air velocity has to be between 10-20 m/s. FIG. 5 shows velocity and collection efficiency results of a CFD simulation at different nozzle parameters, namely variation to d2/d1 and x2/d1. As shown, the velocity at the surface decreases with decreasing d2/d1 and with increasing x2/d1, and the collection efficiency has the same effect. In embodiments, the curve shown in FIG. 5 may be used as a nozzle and collector design guide. For example, to achieve a velocity of 20 m/s for d2/d1=2, x2/d1 has to be equal to 10 (see dashed line in FIG. 5). At those conditions, the collection efficiency is ~60%. Furthermore, for each operating condition a different curve is generated. Accordingly, the curves shown in FIG. 5 may be used to configure a cavity that preserves a specific amount of liquid, such as a buffer. Furthermore, by configuring the dimension d3 the surface tension of the liquid surface may be controlled. In particular, as d3 decreases the surface tension forces increase and make it more difficult for the liquid to escape.

Collector Geometry and Operating Conditions

The geometry of the collector may also be engineered to control particle wall losses, particle bounce, particle collection, manufacturability and ease of use. There are multiple parameters in the geometry that are important to the design of the collector. Exemplary embodiments providing the optimization of some of these parameters are provided for the collector embodiments provided in FIGS. 3*a* and 3*b*, and may also be applied universally including to the embodiment shown in FIG. 3*c*.

Nozzle Angle Parameter

The angle of the nozzle, annotated as ($\theta_1$) in FIG. 6, is one of the collector geometry parameters that can impact the efficiency of particle collection. As shown in FIG. 6, at high nozzle angles ($\theta_1$), re-circulation zones (54) are created in the nozzle throat entrance (56) area. This zone results in particle losses at the entrance of the nozzle (56) and prevents these particles from reaching the collection reservoir medium. At lower angles these zones disappear. Manufacturing errors, ledges in the nozzle throat entrance, create similar disturbances in the entrance area of the nozzle throat and amplify the effect of larger angles resulting in a rise in particle loss on walls. FIG. 7 shows the particle losses in relationship to the nozzle angles and can be used in configuring the collector nozzle angle. FIG. 7 also shows how ledges affect losses, which can also be used as a design principle in configuring the collector.

Nozzle Throat Length

The arrangement and geometry of exemplary collector nozzle throats are provided in FIGS. 8*a* and 8*b*. As shown, the nozzle throat (60) length (T) determines the velocity of the air and particle at the nozzle exit (62). A sufficiently long nozzle throat will allow the air to reach a fully developed flow before exiting the nozzle. However, the nozzle should be short enough to reduce the particle velocity at the nozzle exit (62), and thus particle losses. The maximum terminal velocity a particle can reach is that of the gas velocity at the nozzle exit (62). The particle velocity at the nozzle exit (62) is another parameter as it determines the final velocity of the particle at the collection surface (or impaction velocity). In particular, a low velocity will tend to eliminate bounce effects. The optimal length then allows for fully-developed air flow and a minimal particle velocity and losses on walls.

FIGS. 8*a* and 8*b* illustrate the concept for 10 μm particles by showing the CFD calculated particle tracks (64). These big particles have high relaxation times Tp and are unable to adapt to fast flow changes caused by changing flow directions in the nozzle throat entrance (68). In the shorter nozzle throat (FIG. 8*a*) (T/d1=2.25; where T is the nozzle throat length), the particles tracks switch sides (66) but do not intercept the wall. This is not the case in the longer nozzle (FIG. 8*b*) (T/d1=8.89) where the particles intercept the wall (69) resulting in efficiency losses. The terminal particle velocity is proportional to the gas velocity. Only 1 μm particles reach the terminal velocity. Considering that a low impaction velocity is required, in this embodiment a nozzle length of T/d1=2.25 would be chosen. Although this is dependent on the flow rate of choice, it will be understood that the design principles still apply for all operating flow rates.

Nozzle Diameter and Operating Pressure

Determining the flow rate of the collector may also be used in configuring the overall design of the sample collection system. For example, in embodiments it affects the design of the pre-collector assembly (or patient interface as discussed below). Assuming an appropriate flow rate is determined using the criteria discussed below then the diameter of the nozzle can be set according to certain rules.

The nozzle diameter (d1) has the largest effect on impaction velocity. A low impaction velocity (vi·dp<5), where vi is particle velocity and dp is the particle diameter, is required to eliminate particle bounce: the larger the diameter the lower the impaction velocities (at a constant volumetric flow rate). In some cases, where low velocities are undesirable, as described below, vi.dp can be within at most an order of magnitude of 5 to control particle bounce. Particle bounce results in loss of collection efficiency. If the velocities are too low, it can result in a loss of collection efficiency since the particles can follow the air stream and exit the collector without being driven into the collection reservoir medium. Therefore, particle impaction velocity and collection efficiency may be balanced to obtain the nozzle diameter. For example, FIG. 9 shows the region of operating diameters for flow rates of 5 and 6.5 liters per minute.

Nozzle-to-Plate Distance

The nozzle to plate distance, $x1/d1$, has no influence on particle collection or impaction velocity at the 5 liters per minute operating condition, when the ratio is between $1.2 \leq x1/d1 \leq 1.6$. At higher ratios small particles can get entrained in the air flow which results in decreasing collection efficiency.

Adapting Sample Collection System to Transient Cough Flow

Preliminary clinical data show that a significant portion of a patient's expelled material is lost in conventional sample collection designs. Insufficient flow rates along with the lack of a capture mechanism in the pre-collector assembly (or patient interface) cause a significant portion of the cough volume to escape through the outlet of the previous design. (Note, cough flowrates peak at 288 L/min, ~0.1 seconds from the start of a cough, which lasts a total of ~0.5 seconds. The average total volume produced by a patient's cough varies between 1 L in male patients and 0.75 L in female patients. See, e.g., Gupta et al., Indoor Air, 19:517-525, 2009, the disclosure of which is incorporated herein by reference.) Accordingly, in embodiments the sample collection system is configured to the measured cough flowrates. In some embodiments, the sample collection system is configured to increase the flowrate through the collector. In other embodiments, a temporary storage area is provided where the excess cough volume may reside before being drawn by the sample collection system. In still other embodiments, both of the above methods can be used synergistically.

Flow Compensation Using Collector Flow Rate

At the peak cough flow rate of ~300 L/min around 100% of the cough is captured, i.e., if the sample collection system is sampled at a flow rate (Q) of ~300 L/min, it would capture the entire cough. However, since the cough flow rate is non-linear (see Table 1, below) with respect to time, a significant portion of the cough can be captured at lower Q values. The square of the nozzle diameter, d1, defines the critical area of flow and therefore a maximum flow rate (Qmax) through the nozzle. In other words, the diameter, Min d1, required to reach a certain Q is the d1 at which Qmax=Q. The Min d1 is listed in Table 1. For example, at a flowrate of 60 L/min, 40% of the cough volume can be captured, and a Min d1 of 2.5 mm is required to achieve that flowrate.

TABLE 1

Design Table for determining the Minimum d1 required to capture a certain percentage of a patient's cough volume.

| Q (lpm) | Min d1 (mm) | Percent captured cough volume |
|---|---|---|
| 0 | 0 | 0% |
| 12 | 1.1 | 9% |
| 30 | 1.8 | 20% |
| 60 | 2.5 | 40% |
| 120 | 3.6 | 73% |
| 180 | 4.4 | 92% |
| 240 | 5.1 | 98% |
| 300 | 5.7 | 100% |

Flow Compensation Using the Pre-Collector Assembly

Accordingly in embodiments, adaptation of the sample collection system to cough flowrates is accomplished by creating a temporary storage that allows excess volume that cannot be directed to the sample reservoir of the sample collection system to be stored and drawn at a rate equal to the flowrate of the collector. As previously described, the sample collection system can be composed of two major parts: the pre-collector assembly (or patient interface), and the collector, as shown in FIG. 1 and FIG. 10. In some embodiments, the pre-collector assembly (PCA) is configured to create a temporary storage whereby the excess cough volume resides before being drawn by the collector. In such embodiments the PCA (70) has one or more of the following specifications:

It can be disposable after use.

It includes an inlet (72) that interfaces to an external opening of the respiratory tract. The inlet interface (72) creates a seal and allows a cough, sneeze, breath or any other aerosol output of the respiratory tract to be directed towards the sample collection system. In one embodiment, the inlet can be a mouthpiece. In another embodiment, the inlet can be a mask. In yet another embodiment, the inlet can be a nosepiece that draws exhaled breath through the nostrils.

Includes a mechanism of managing flow from the patient. During the exhalation phase, a mechanism whereby the output from the respiratory tract at flowrate, Q, is directed to the collector (76) operating at Q1 and the remaining flow, Q2, to a reservoir (78) with no losses to the external environment. In some embodiments, a mechanism is provided whereby captured air in the reservoir is prevented from being drawn by the patient through the inlet (72) during inhalation. In other embodiments, a mechanism is provided whereby the captured exhaled volume is directed towards the collector (76) at a rate of Q1 during inhalation.

In one such embodiment, shown in FIG. 10a, the PCA mechanism consists of two one-way valves (80, 82). In one embodiment, the one-way valves (80, 82) can consist of silicon rubber attached to a surface that restricts its bending to one direction. In another embodiment, the one-way valves (80, 82) can be electronically controlled. In such an embodiment, upon exhalation, the PCA directs the cough volume through a one-way valve (82) to an expandable reservoir placed at an angle to the direction of main flow from patient (90). In one embodiment, this reservoir can be an inflatable plastic bag that provides no resistance as it is being inflated. In another embodiment, this reservoir is made of an elastic material similar in nature to a balloon, such that an elastic resistance is provided. During inhalation, the same one-way valve (82) prevents the captured exhaled volume from exiting the reservoir and directs it towards the collector (76).

During the same phase, the other one-way valve (80) permits the patient to inhale of ambient air through the PCA (70).

In another such embodiment, shown in FIG. 10*b*, the mechanism is similar to that described above, with the exception that only a single one-way valve (82) is used. This prevents the patient from breathing in while using the PCA. The patient is instead instructed to breath in by removing the PCA.

In yet another such embodiment, shown in FIG. 10*c*, the mechanism is similar to that described above, whereas the reservoir (78) is placed in-line to the direction of main flow from the patient.

The one-way valve operates as a gate that opens to allow air in one direction in reaction to a force. In one embodiment, the force that opens the valve is the air exiting the patient. In another embodiment, the force that opens a valve is supplied through a spring controlled by the patient using a button placed on the PCA.

Is made of plastic parts that are static dissipative to avoid surface charges that can attract particles to the PCA walls and cause losses in the system.

It is handheld

The volume of the reservoir (78) varies based on two parameters: the number of coughs it has to store before the patient can fill it up again and the flow rate of the collector (76)

Conventional sample collection designs have attempted to circumvent the need to achieve a PCA that manages airflow. For example, Fennelly et al. use a metal canister that is not disposable and has to be autoclaved between runs. (See, e.g., Fennelly, et al., American Journal of Respiratory and Critical Care Medicine, 186(5):450-457, 2012, the disclosure of which is incorporated herein by reference.) In such conventional devices the collector is placed within the canister. Furthermore, unlike the described invention where all exhaled output is directed to the collector, the conventional canister provides a filtered outlet to allow excess air to escape. Finally, unlike the current designs where the reservoir is expandable, the canister has a fixed footprint, which excludes it from being handheld. In another attempt, Lindsley et al. use a metal chamber equipped with an expanding piston that accommodates the extra air from the patient. (See, e.g., Lindsley, et al., PloS one, 5(11):e15100, 2010, the disclosure of which is incorporated herein by reference.) Here again the same issues exist except that Lindsley's system directs all the air towards the collection device. However, to prevent backflow Lindley uses a manual cork after coughing to prevent the air from escaping the metal piston chamber.

Other prior art includes methods using filtration such as the Pneumoniacheck™. (See, e.g., Scholz et al. Journal of Medical Devices, 4(4):041005, 2010, the disclosure of which is incorporated herein by reference.) Unlike the embodiments described herein, these filtration devices are limited to a filter surface. Furthermore, the filter surface area determines the flowrate through the filtration device while, as described above, in embodiments the collection reservoir of the sample collection system does not affect the overall flowrate of the collector.

Pre-Collector Assembly as Size Separator

The pre-collector assembly (or patient interface) has another function: a screening device for particles that reach the collector. The collector is designed to collect particles of size (dp) in the collection reservoir where $dp,c<dp$. However, in certain disease states, the goal of the sample collection system is to collect particles of size (dp) where $dp,c<dp<dp,1$. The collector in and of itself cannot achieve this. The pre-collector assembly (or patient interface) can be designed to exclude particles of $dp>dp,1$ from reaching the collection reservoir of the collector. Therefore, in embodiments the sample collection system can be designed to collect particles of size (dp), where $dp,c<dp<dp,1$. The size of a cough aerosol has been linked to its site of origination: particles with diameters $(dp)<5$ µm are from the lower respiratory tract (LRT), while those with $dp>10$ µm are from the upper respiratory tract (URT). (See, e.g., Fennelly et al., American Journal of Respiratory and Clinical Care Medicine, 169(5):604-609, 2004, the disclosure of which is incorporated herein by reference.) In diseases where exclusively LRT sample is needed to obtain a diagnosis, such as Pneumonia, the PCA includes a low pass filter mechanism, as described above. In this case, the PCA preferentially excludes particles with $dp>5$ µm. Alternatively, only very large particle debris such as sputum debris can be blocked in the pre-collector assembly.

Figure 11A:
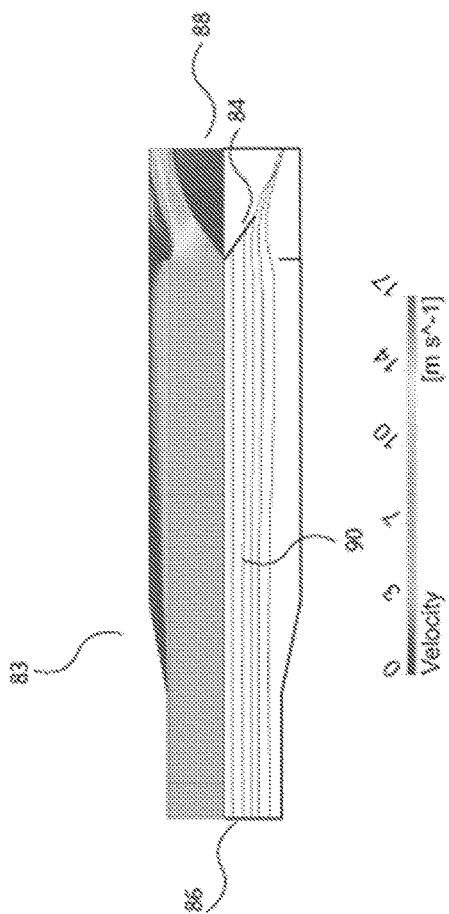
FIG. 11a provides a schematic of a pre-collector assembly cross-section whereby a one-way valve acts as a low-pass filter, overlaid on the schematic is CFD data driven 10 μm particle tracks as well as a contour of the air velocity in accordance with embodiments of the invention.
Figure 11B:
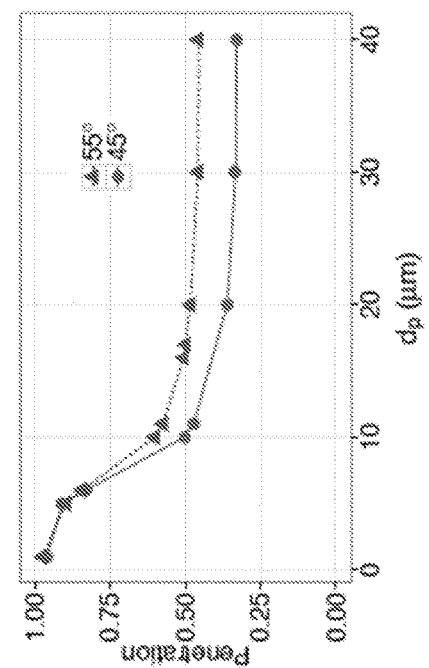
FIG. 11b provides a data graph showing particle penetration as a function of particle diameter for two different valve bend angles in accordance with embodiments of the invention.

In one embodiment, shown in FIG. 11A, a low-pass filter mechanism (83) comprising a one-way valve (84) is placed in the path of the flow originating at the patient (86) and ending at the collector inlet (88). The one-way valve is configured to bend (88) during exhalation. The bend angle varies depending on the flow produced by the patient as well as intrinsic properties of the valve, such as the type of material and geometric dimensions. In a CFD simulation (FIG. 11B), where the average (2 lps) flowrate generated by a patient cough is studied, particles (90) are captured on the valve surface. In this embodiment, the angle is chosen to be 55 degrees to reduce the aerodynamic forces acting on it to $<0.7$ N, and the valve is shown to allow 30% of the particles with $dp>20$ µm to go through the PCA and reach the collector (Penetration—P, see FIG. 11B). For $dp=10$ µm, P—50% make it past the valve to the collector—the particle tracks (90) show a subset of the 10,000 particles used to calculate P in FIG. 11B. As described, the geometry can be refined to decrease the penetration, P. One such modification is to change the valve material to allow for a smaller bend angle. A 10 degree drop (from 55 degrees to 45 degrees) in the bend angle decreases the penetration of particles $>10$ µm by ~10% (see FIG. 11). Another modification would be to reduce the valve diameter causing the velocity of the air to increase, which in turn reduces penetration. Another modification would be to reduce the distance between the valve and the inlet, giving the particles less time to react to the changing flow around the valve, which in turn reduces penetration.

Although embodiments are described above with respect to some diseases, in diseases where both URT and LRT samples are beneficial to obtain a diagnosis, such as Influenza, the PCA is designed to avoid exclusion of particle sizes. Although some exclusion can remain in terms of very large sputum matter emanating from the patient.

Ability to Collect DNA from Broken-Up Cells

Figure 12A:
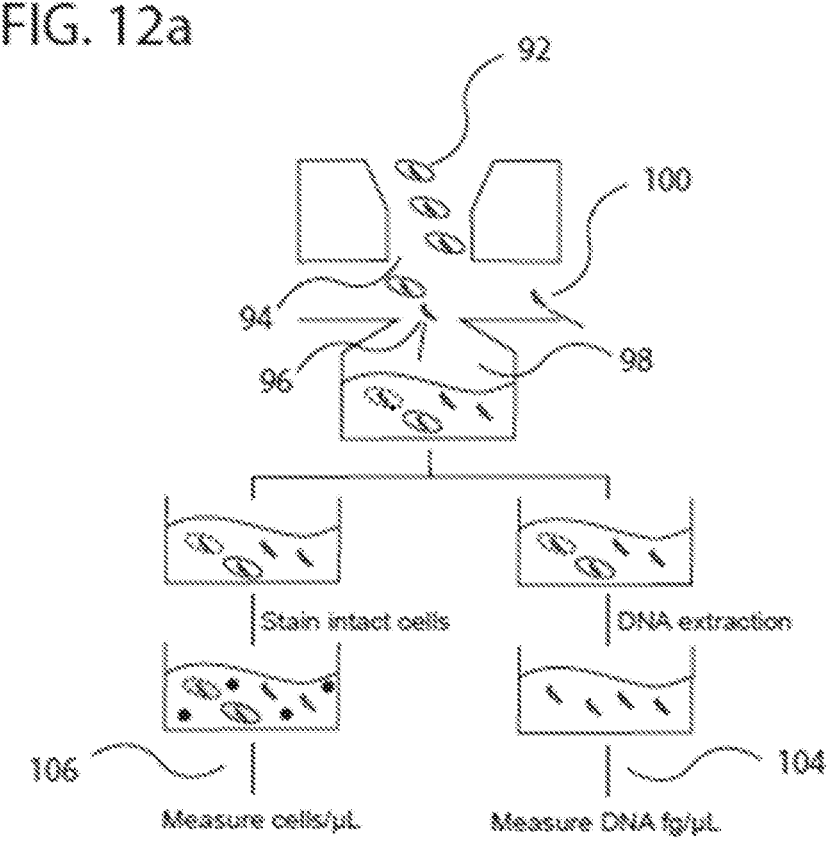
FIG. 12a provides a schematic of a collector embodiment showing cell break-up and collection and indicating the measurement process for determining the ratio of DNA to cells in the collection reservoir in accordance with embodiments of the invention.

Previously it has been demonstrated that bacterial cells are lysed in an aerodynamic shock. (See, e.g., Sislian et al., Chemical Engineering Science, 65(4):1490-1502, 2010, the disclosure of which is incorporated herein by reference.) Referencing FIG. 12A, it has been shown that a fraction of intact cells (92) pass through the collector nozzle (94) at conditions of shock break up. Collection of the cellular components (96), specifically genomic DNA, following break-up has never been shown in conventional devices. However, once the cell is broken-up, the cellular components can either be directed toward the collection reservoir (98) or follow the path of air (100). To demonstrate the collection of genomic DNA from the lysed cells in embodiments, the total mass of DNA is compared to the total number of cells in the collection buffer. As shown in FIG. 12A, both measurements of the DNA mass (104) and the number of cells (106) are conducted on the same sample following the collection experiment. Once the cell concentration (cells/μL) and the mass concentration (fg/μL) are measured, the mass of DNA per cell (fDNA in fg/cell) can then be calculated. *E. coli* contains 5 fg/cell of genomic DNA per cell. In the limit where no cells are lysed, genomic DNA is fully contained in the cells and therefore the measured fDNA should be equal to 5 fg/cell. As the value of fDNA increases, more genomic DNA is extra-cellular, indicating collection of the cellular components of the broken up cells.

Figure 12B:
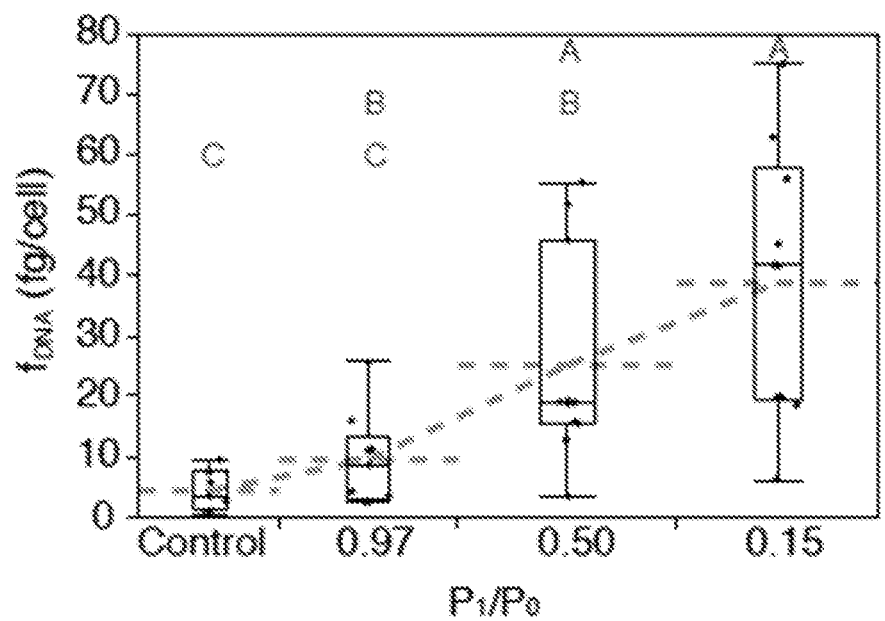
FIG. 12b provides a data graph showing the increase in extra-cellular DNA due to cell break-up at higher P1/P0 in accordance with embodiments of the invention.

FIG. 12B shows calculated fDNA data in a box-plot for four different experiments, each repeated n times. Using the ANOVA test, p-values are calculated to statistically analyze the data. The fDNA of a cell suspension was performed. An average of 4.5 fg/cell is calculated for the control experiments, which is statistically equivalent to the 5 fg/cell expected for *E coli*. This data establishes that: 1) the measurement method is valid and produces results that mimic the known mass of genomic DNA in *E. coli*, and 2) the starting culture does not contain extra-cellular genomic DNA. In the next three experiments, cells are nebulized and collected at three different pressure conditions—where P1 and P2 are the pressure downstream and upstream of the collector nozzle (94), respectively—in the collector: P1/P0=0.97 (n=9), 0.50 (n=11), and 0.15 (n=10). Aerodynamic shocks are created at P1/P0<0.53; therefore, no break-up is expected at P1/P0=0.97 and break-up for the other two conditions. At the condition where no shock exists, the average fDNA is 9.6 fg/cell, slightly higher but not significantly different from the control (p=0.19). At $\chi$=0.50 and 0.15, fDNA=25.2 fg/cell and 38.7 fg/cell, respectively. For the two conditions with aerodynamic shock, both fDNA values are significantly higher than the control (p<0.05), though the fDNA for the two conditions was not significantly different from each other (p=0.21). The letters A, B and C in FIG. 12B indicate which distributions are statistically distinguishable: if two distributions have the same letter then they are considered statistically equal. As shown, a statistically significant amount of cellular components is collected at lower P1/P0 in relation to higher P1/P0, indicating that the shock breaks up the cells and that the cellular components are concentrated in the collection reservoir.

Mechanism of Creating Flow Through Collector

Some embodiments of the sample collection system include establishing a flow through the collector.
 a) In one embodiment of the sample collection system, the positive pressure produced by the patient drives the flow through the collector.
 b) In another embodiment, the pre-collector assembly reservoir provides the positive pressure to drive the flow through the collector. In one such embodiment, the reservoir is made of an elastic material, akin to a balloon, that can be inflated by the patient's exhaled matter. Exhaled matter delivered to the elastic reservoir is impeded from backflow by a one-way valve. The inflation of the elastic reservoir stores the work of the patient's exhalation as potential energy. The elastic reservoir then drives the flow through the collector by converting the potential energy to kinetic energy of flow.
 c) In another embodiment, a vacuum pump placed downstream of the collector drives the flow through the collector. In yet another embodiment, the pump can be a rechargeable and portable one. In yet another embodiment, an industrial vacuum line drives the flow.

Positive Control Establishing Adequate Collection

In one embodiment of the sample collection system a positive control is included to ensure that exhaled matter was collected. The positive control can be a test for a specific signature that could be a specific organic, inorganic or biological molecule. The test can also be for a specific signature of a fragment or intact live or dead bacterial cell, virus, or cell originating from the subject. The requirement is that the specific signature is present in all humans. One embodiment of such a specific signature is the bacterium *S. Mitis* and any components thereof that is present in the oral cavity of all patients. Another embodiment of the specific signature is the molecule Glutathione that is present in alveolar lining fluid. One embodiment of such a test, is a real-time readout such as a change of color that indicates that enough exhaled matter was collected. In another embodiment of such a test, a readout of the specific signature is indicated when the actual diagnostic device tests for the analyte. The positive control can also be a physical measurement. In one embodiment, the positive control can be a measurement of how much volume was expelled from the patient.

Humidity Control

Some particles emitted from the patient are in the form of liquid droplets that contain the analyte. The size of these droplets depends on the humidity in the sample collection system. In one embodiment of the sample collection system, placing hydroscopic materials in the PCA lowers the humidity. In one such embodiment, the entire PCA can be made of hygroscopic plastics such as Nylon. In another such embodiment, hygroscopic materials such as silica gel can be placed in various parts of the PCA. One such area of the PCA where such materials can be placed is the reservoir described in more detail in previous sections. In another embodiment, clean dry air from environment is allowed to mix with the patient's output.

EXEMPLARY EMBODIMENTS

Example 1

Example Embodiment of the Sample Collection System

FIG. 13 shows one embodiment of a sample collection system that combines multiple aspects. The sample collection system (109) consists of a pre-collector assembly (108) and a collector (110). The pre-collector assembly includes a mechanism of managing flow from the patient depicted in the embodiment shown in FIG. 10*c*. Furthermore, in the embodiments the pre-Collector assembly includes a mechanism of excluding droplets >10 μm with an efficiency of >50% as depicted in FIG. 11. In this embodiment the pre-collector assembly consists of a T-junction (112) with three ends (114, 116, 118)—one end connecting to the mouthpiece (114), the second to a bag (116), and the third to the collector (118), although the bag and mouthpiece are not shown in FIG. 13. In addition, the embodied pre-collector assembly includes a one-way valve (120), which is made of a silicone flap (122) that rests on a plastic ring (123), which is inserted into the T-junction. The flap can only open in one direction bending its edges towards the collector (110) when the patient flow encounters the valve. The collector (110) used in this embodiment does not include a cartridge module. The sample reservoir (124) is the one described in the embodiment of FIG. 4, and the geometry is set using the design rules discussed in relation to FIGS. 6 to 9. The embodiment was tested in clinic on CF patients with confirmed *P. aeruginosa* infections. These patients were confirmed to be positive for *P. aeruginosa* using the gold-standard culture techniques. The exemplary sample collection system in FIG. 13 yields cough positive PCR results in 13 out of 14 patients Example 2

Improvement on Fennelly's Collection System

Figure 14:
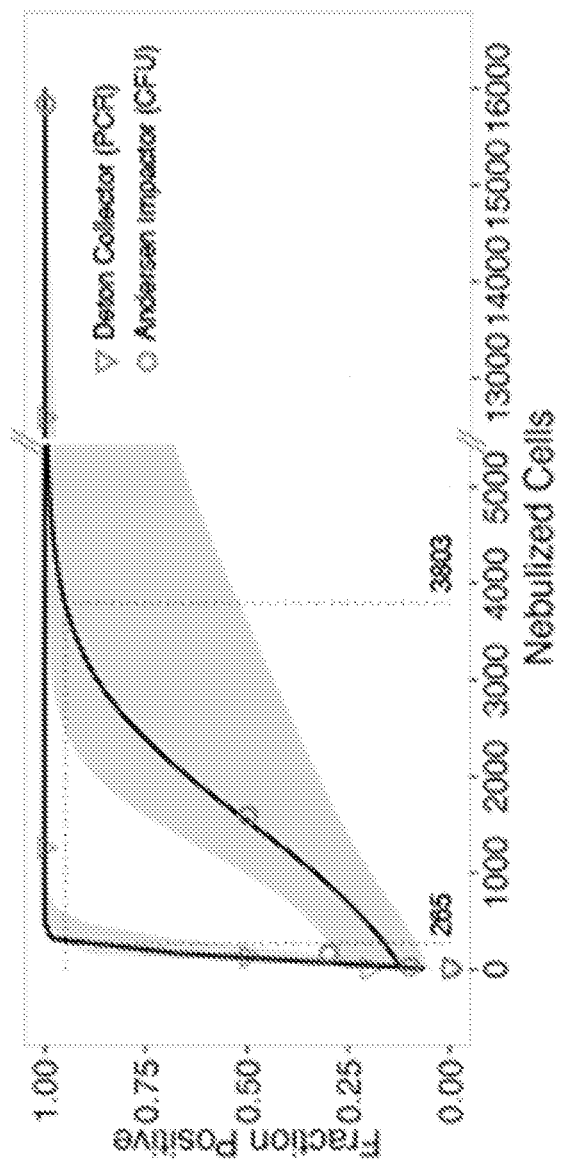
FIG. 14 provides a data graph showing the detection improvement using embodiments of the invention shown in FIG. 13 compared to a prior-art Anderson collector.

The exemplary sample collection system described above can be contrasted with the Andersen impactor, used in Fennelly's collection system, which was developed in 1958 for environmental sampling and, while adept at the collection of bioaerosol, was not designed for diagnostic detection of clinical samples. In particular, it has been shown that deposition of bacteria on selective media, such as 7H11 agar, structurally damages cells and can render up to 99% non-viable (See, e.g., Stewart et al., Applied and Environmental Microbiology, 61(4):1232-1239, 1995, the disclosure of which is incorporated herein by reference.) Furthermore, efficient extraction of PCR-ready DNA is impractical due to the large area of the agar plate. Finally, the setup is designed for research use and is impractical for clinical use; the impactor is placed in a large (~20" by 8") metal chamber that hinders transport and sterilization. Exemplary embodiments of the sample collection system and the Andersen impactor were tested in a lab by sampling aerosolized *E. coli* from a common reservoir. FIG. 14 shows that the limit of detection of the exemplary sample collection system with 35 cycle PCR is at least 10× lower (better limit of detection) than that of the Andersen impactor with culture.

DOCTRINE OF EQUIVALENTS

As can be inferred from the above discussion, the above-mentioned concepts can be implemented in a variety of arrangements in accordance with embodiments of the invention. Accordingly, although the present invention has been described in certain specific aspects, many additional modifications and variations would be apparent to those skilled in the art. It is therefore to be understood that the present invention may be practiced otherwise than specifically described. Thus, embodiments of the present invention should be considered in all respects as illustrative and not restrictive.

What claimed is:

1. A biological sample collector system comprising:
   a pre-collection assembly configured to engage with a patient such that the entirety of the outflow of breath from the patient including any biological particulates contained therein is captured within the collector system;
   a sample reservoir possessing a reservoir entrance and defining a volume having therein a sample medium for entraining the target biological particulates in the sample medium to form a sample analyte suitable for diagnostic analysis;
   a collector in fluid communication between the pre-collection assembly and the sample reservoir, the collector having a collector inlet at a first end thereof and having at its terminating end a fluid focusing nozzle, the fluid focusing nozzle having a nozzle entrance, an exit, and a throat spanning therebetween;
   wherein the ratio of the throat length of the nozzle to the internal diameter of the nozzle is configured such that the biological particulates do not intercept an internal wall of the throat;
   wherein said target biological particulates are directed into said sample reservoir such that efficient transfer of the target biological particulates into the sample medium is obtained; and
   wherein at least a portion of the outflow of breath flows through said pre-collection assembly and into said collector in any single breath, and wherein the remainder of the outflow of breath is temporarily stored within said pre-collection assembly.

2. The system of claim 1, wherein an angle is formed between the nozzle entrance and the collector upstream of said nozzle entrance, wherein the nozzle entrance is configured such that recirculation zones are prevented from forming in the nozzle entrance, wherein the throat has a length configured to prevent the biological particulates from reaching their terminal velocity, and wherein the nozzle is defined by an internal diameter and wherein the internal diameter is configured to reduce particle bounce and increase collection at a specified flow rate.

3. The system of claim 1, wherein the sample reservoir is incorporated into a cartridge module in fluid connection with the collector, the cartridge module being removable from said collector system and being configured to cooperatively engage with an input of a diagnostic analyzer.

4. The system of claim 3, wherein the cartridge module containing the sample reservoir comprises a self-sealing mechanism configured to isolate the sample medium from the external atmosphere.

5. The system of claim 3, wherein the sample reservoir includes a mechanism for ejecting the sample medium into the input of the diagnostic analyzer.

6. The system of claim 1, wherein the sample medium contained within the sample reservoir takes a form selected from the group consisting of a tablet, a pelletized salt, a liquid, a film, and a gel.

7. The system of claim 1, wherein the reservoir entrance is disposed opposite the fluid focusing nozzle.

8. The system of claim 7, wherein an exposed surface of the sample medium contained within the sample reservoir is dimensioned to be on the order of the diameter of the nozzle.

9. The system of claim 7, wherein the sample medium is a liquid and the sample reservoir further comprises an airspace defining a cross-sectional length between the exit of the nozzle and the exposed surface of sample medium, and wherein the cross-sectional length of the airspace, the internal diameter of the nozzle and the distance between the end of the nozzle and the exposed surface of the sample medium are configured such that the velocity of the outflow at the exposed surface of the sample medium is less than 20 m/s.

10. The system of claim 2, wherein the ratio of the distance from the end of the nozzle and the exposed surface of the sample medium and the nozzle diameter is greater or equal to 1.2 and less than or equal to 1.6.

11. The system of claim 2, wherein the angle formed between the entry of the fluid focusing nozzle and the collector upstream of said nozzle is less than 30° such that recirculation zones are prevented from forming in the nozzle entrance.

12. The system of claim 2, wherein the ratio of the length of the nozzle to the diameter of the nozzle is less than 2.25.

13. The system of claim 2, wherein the nozzle diameter is configured such that the velocity of the biological particulates at the surface of the sample medium multiplied by the particle diameter is less than 50 to control biological particulate bounce against the surface of the sample medium such that the collection efficiency of the particle size of interest is greater than 0.9.

14. The system of claim 1, wherein the collector has a specified flow capacity, and wherein the pre-collector assembly further comprises a temporary storage volume configured to capture any portion of the outflow of breath from the patient that exceeds the flow capacity of the collector.

15. The system of claim 14, wherein the temporary storage volume includes a one-way valve mechanism whereby the breath captured in the temporary storage volume is prevented from being inhaled by the patient and releases the captured breath into the collector during an inhalation by the patient.

16. The system of claim 15, wherein the one-way valve is triggered by one of either an automated mechanism or manually by the patient.

17. The system of claim 15, wherein the pre-collector assembly further comprises a second one-way valve that allows an inhalation of breath by the patient through the pre-collector assembly.

18. The system of claim 14, wherein the temporary storage volume is formed of an elastic material, such that the temporary storage volume stores at least a portion of both the volume of the outflow of breath and the work of the outflow of breath as potential energy, and wherein the potential energy may be converted to a kinetic flow by releasing said stored portion of the outflow of breath into the collection system.

19. The system of claim 1, wherein the pre-collector assembly further comprises a filter mechanism for filtering out biological particulates of greater than a target size from said target biological particulates.

20. The system of claim 19, wherein the filter mechanism comprises a one-way valve configured to bend during exhalation by a patient such that particulates greater than the target size impact the valve and are prevented from entering the collector.

21. The system of claim 1, wherein the collector further comprises an aerodynamic impactor having first and second ends and defining a fluid path therein, and wherein the aerodynamic impactor applies an inertial deceleration force to the gaseous sample, and wherein the magnitude of the inertial force can be varied such that at a low inertial force any biological particulates within the sample are passed through the impactor intact and that at an inertial force above a threshold any biological particulates within the sample are lysed to release the internal components thereof.

22. The system of claim 21, wherein the internal components of the target biological particulates contain DNA.

23. The system of claim 1, further comprising a positive control configured to provide an indication that a sufficient volume of the outbreath of the patient has been collected.

24. The system of claim 23, wherein the positive control is selected from the group consisting of an indicator for a signature biological material and a physical measurement of the outflow of breath from the patient.

25. The system of claim 1, wherein the pre-collector assembly further comprises a humidity control system configured to prevent particle growth.

* * * * *